(12) United States Patent
Ritter et al.

(10) Patent No.: US 8,801,725 B2
(45) Date of Patent: Aug. 12, 2014

(54) INSTRUMENTS AND METHODS USED WHEN REPAIRING A DEFECT ON A TISSUE SURFACE

(75) Inventors: Robin Ritter, Cedar Park, TX (US); Victor Zaporojan, Austin, TX (US); Jizong Gao, Cedar Park, TX (US)

(73) Assignee: Zimmer Orthobiologics, Inc., Austin, TX (US)

( * ) Notice: Subject to any disclaimer, the term of this patent is extended or adjusted under 35 U.S.C. 154(b) by 1019 days.

(21) Appl. No.: 12/045,416

(22) Filed: Mar. 10, 2008

(65) Prior Publication Data

US 2009/0228031 A1  Sep. 10, 2009

(51) Int. Cl.
- *A61F 2/00* (2006.01)
- *A61B 17/16* (2006.01)
- *A61B 17/17* (2006.01)

(52) U.S. Cl.
CPC ............ *A61B 17/1635* (2013.01); *A61B 17/17* (2013.01)
USPC .......................................... 606/102; 606/130

(58) Field of Classification Search
CPC ........... A61F 2/4657; A61F 2002/4663; A61F 2002/4664; A61F 2002/4668
USPC ............................. 606/96, 102, 130, 167, 170
See application file for complete search history.

(56) References Cited

U.S. PATENT DOCUMENTS

| | | | |
|---|---|---|---|
| 493,730 A * | 3/1893 | MacKenzie | 606/179 |
| 1,405,720 A | 2/1922 | Scott | |
| 1,567,910 A | 12/1925 | Franz et al. | |
| 1,703,154 A | 2/1929 | Lanzkron | |
| 1,842,573 A | 1/1932 | Treek | |
| 1,984,839 A | 12/1934 | Murray | |
| 2,573,462 A | 10/1951 | Lindsey | 408/86 |
| 3,564,947 A | 2/1971 | Maier | |
| 3,564,948 A | 2/1971 | Pomernacki | |
| 3,848,601 A | 11/1974 | Ma | |
| 3,971,273 A | 7/1976 | Peters et al. | |
| 4,010,737 A | 3/1977 | Vilaghy et al. | |

(Continued)

FOREIGN PATENT DOCUMENTS

| | | |
|---|---|---|
| AU | 4922296 A | 9/1996 |
| DE | 2411618 A1 | 4/1975 |

(Continued)

OTHER PUBLICATIONS

Barber et al. (2006), "*Osteochondral Repair System*," www.obi.com, pp. 1-17.

(Continued)

*Primary Examiner* — Darwin Erezo
*Assistant Examiner* — Martin T Ton
(74) *Attorney, Agent, or Firm* — Schwegman Lundberg & Woessner, P.A.

(57) ABSTRACT

An instrument for determining the proper orientation for repairing a defect site on a tissue surface generally comprises a shaft, a plurality of probes operatively coupled to the shaft, and at least one indicator operatively coupled to the plurality of probes. The probes are configured to extend beyond a first end of the shaft and are movable relative the shaft. The at least one indicator is configured to display the displacements of the probes relative to the first end so that the displacements of the probes may be compared. A method of using the instrument when repairing a defect on a tissue surface is also disclosed.

30 Claims, 10 Drawing Sheets

(56) References Cited

U.S. PATENT DOCUMENTS

| | | | |
|---|---|---|---|
| 4,250,892 A * | 2/1981 | Dolhay et al. | 600/571 |
| 4,589,206 A | 5/1986 | Marcoux | |
| 4,706,659 A | 11/1987 | Matthews et al. | |
| 5,067,964 A | 11/1991 | Richmond et al. | |
| 5,115,704 A | 5/1992 | Hyman | |
| 5,139,520 A | 8/1992 | Rosenberg | |
| 5,152,791 A | 10/1992 | Hakamatsuka et al. | |
| 5,184,926 A | 2/1993 | Hemmings | |
| 5,197,833 A | 3/1993 | Mayer et al. | |
| 5,207,681 A | 5/1993 | Ghadjar et al. | |
| 5,328,722 A | 7/1994 | Ghanayem et al. | |
| 5,341,816 A | 8/1994 | Allen | |
| 5,345,927 A * | 9/1994 | Bonutti | 600/207 |
| 5,362,166 A | 11/1994 | Yamamoto et al. | |
| 5,368,051 A | 11/1994 | Dunn et al. | |
| 5,370,692 A | 12/1994 | Fink et al. | |
| 5,423,823 A | 6/1995 | Schmieding | |
| 5,425,490 A | 6/1995 | Goble et al. | |
| 5,443,468 A | 8/1995 | Johnson | |
| 5,575,798 A * | 11/1996 | Koutrouvelis | 606/130 |
| 5,587,912 A | 12/1996 | Andersson et al. | 364/468 |
| 5,591,234 A | 1/1997 | Kirsch | |
| 5,632,745 A | 5/1997 | Schwartz | |
| 5,632,747 A | 5/1997 | Scarborough et al. | |
| 5,718,707 A | 2/1998 | Mikhail | |
| 5,771,310 A | 6/1998 | Vannah | |
| 5,782,835 A | 7/1998 | Hart et al. | |
| 5,788,713 A * | 8/1998 | Dubach et al. | 606/130 |
| 5,810,887 A * | 9/1998 | Accorti et al. | 607/122 |
| 5,860,946 A | 1/1999 | Hofstatter | |
| 5,876,452 A | 3/1999 | Athanasiou et al. | |
| 5,885,293 A * | 3/1999 | McDevitt | 606/80 |
| 5,899,860 A * | 5/1999 | Pfeiffer et al. | 600/424 |
| 5,904,717 A | 5/1999 | Brekke et al. | |
| 5,919,196 A | 7/1999 | Bobic et al. | 606/86 |
| 5,921,987 A | 7/1999 | Stone | |
| 6,074,394 A * | 6/2000 | Krause | 606/86 R |
| 6,110,178 A | 8/2000 | Zech et al. | 606/96 |
| 6,146,385 A | 11/2000 | Torrie et al. | |
| 6,231,608 B1 | 5/2001 | Stone | |
| 6,242,247 B1 | 6/2001 | Rieser et al. | |
| 6,251,143 B1 | 6/2001 | Schwartz et al. | |
| 6,270,503 B1 | 8/2001 | Schmieding | |
| 6,306,142 B1 | 10/2001 | Johanson et al. | |
| 6,358,253 B1 | 3/2002 | Torrie et al. | |
| 6,375,658 B1 | 4/2002 | Hangody et al. | |
| 6,395,011 B1 | 5/2002 | Johanson et al. | |
| 6,459,948 B1 | 10/2002 | Ateshian et al. | 700/117 |
| 6,488,033 B1 | 12/2002 | Cerundolo | |
| 6,511,511 B1 | 1/2003 | Slivka et al. | 623/23.75 |
| 6,520,964 B2 | 2/2003 | Tallarida et al. | |
| 6,530,928 B1 | 3/2003 | Frei et al. | 606/99 |
| 6,582,438 B2 | 6/2003 | DeMayo | |
| 6,591,581 B2 | 7/2003 | Schmieding | |
| 6,592,588 B1 | 7/2003 | Bobic et al. | |
| 6,610,067 B2 | 8/2003 | Tallarida et al. | |
| 6,656,195 B2 | 12/2003 | Peters et al. | |
| 6,679,917 B2 | 1/2004 | Ek | |
| 6,767,354 B2 | 7/2004 | Johanson et al. | |
| 6,793,429 B2 | 9/2004 | Arrison | |
| 6,852,114 B2 | 2/2005 | Cerundolo | |
| 6,858,042 B2 | 2/2005 | Nadler et al. | 623/11.11 |
| 6,988,015 B1 | 1/2006 | Schopf et al. | |
| 6,998,418 B1 | 2/2006 | Sung et al. | |
| 7,029,479 B2 | 4/2006 | Tallarida et al. | |
| 7,048,477 B2 | 5/2006 | Abrams | |
| 7,160,305 B2 | 1/2007 | Schmieding | |
| 7,264,634 B2 | 9/2007 | Schmieding | |
| 7,371,260 B2 | 5/2008 | Malinin | |
| 7,416,371 B2 | 8/2008 | Scott et al. | |
| 7,548,865 B2 | 6/2009 | Schmieding | |
| 7,550,007 B2 | 6/2009 | Malinin | |
| 7,563,266 B2 | 7/2009 | Camino et al. | |
| 7,572,291 B2 | 8/2009 | Gil et al. | |
| 7,591,820 B2 | 9/2009 | Schmieding et al. | |
| 7,608,098 B1 | 10/2009 | Stone et al. | |
| 7,666,230 B2 | 2/2010 | Orban et al. | |
| 7,758,583 B2 | 7/2010 | Gil et al. | |
| 7,758,643 B2 | 7/2010 | Stone et al. | |
| 7,776,043 B2 | 8/2010 | Nycz et al. | |
| 7,833,269 B2 | 11/2010 | Nycz et al. | |
| 7,862,567 B2 | 1/2011 | Schmieding | |
| 7,875,032 B2 | 1/2011 | Lyons | |
| 7,879,040 B2 | 2/2011 | Bharadwaj | |
| 7,887,546 B2 | 2/2011 | Gil | |
| 7,905,904 B2 | 3/2011 | Stone et al. | |
| 7,909,851 B2 | 3/2011 | Stone et al. | |
| 7,909,873 B2 | 3/2011 | Tan-Malecki et al. | |
| 7,914,539 B2 | 3/2011 | Stone et al. | |
| 7,955,335 B2 | 6/2011 | Gil et al. | |
| 7,955,336 B2 | 6/2011 | Gil et al. | |
| 7,985,230 B2 | 7/2011 | Gil et al. | |
| 7,997,174 B2 | 8/2011 | Gil et al. | |
| 8,034,090 B2 | 10/2011 | Stone et al. | |
| 8,048,079 B2 | 11/2011 | Iannarone | |
| RE43,714 E | 10/2012 | Nadler et al. | |
| 8,435,305 B2 | 5/2013 | Lozier et al. | |
| 2003/0167062 A1 | 9/2003 | Gambale et al. | |
| 2003/0171810 A1 | 9/2003 | Steiner | |
| 2004/0039400 A1 | 2/2004 | Schmieding et al. | |
| 2004/0193154 A1 | 9/2004 | Leatherbury et al. | |
| 2004/0230194 A1 | 11/2004 | Urbanski et al. | |
| 2004/0230303 A1 | 11/2004 | Gomes et al. | 623/16.11 |
| 2005/0013872 A1 | 1/2005 | Freyman | |
| 2005/0021044 A1* | 1/2005 | Stone et al. | 606/102 |
| 2005/0038520 A1 | 2/2005 | Bienette et al. | |
| 2005/0080435 A1* | 4/2005 | Smith et al. | 606/151 |
| 2005/0137600 A1 | 6/2005 | Jacobs et al. | |
| 2006/0131906 A1 | 6/2006 | Maurer et al. | |
| 2006/0247790 A1 | 11/2006 | McKay | |
| 2007/0043376 A1 | 2/2007 | Leatherbury et al. | |
| 2007/0135917 A1 | 6/2007 | Malinin | |
| 2007/0135918 A1 | 6/2007 | Malinin | |
| 2007/0149982 A1 | 6/2007 | Lyons | |
| 2007/0270711 A1 | 11/2007 | Gil et al. | |
| 2007/0299517 A1 | 12/2007 | Davisson et al. | 623/11.11 |
| 2008/0019115 A1* | 1/2008 | Park et al. | 362/29 |
| 2008/0027447 A1 | 1/2008 | Gil et al. | |
| 2008/0051812 A1 | 2/2008 | Schmitz et al. | |
| 2008/0167653 A1 | 7/2008 | Watlington et al. | |
| 2008/0195115 A1 | 8/2008 | Oren et al. | |
| 2008/0200915 A1 | 8/2008 | Globerman et al. | |
| 2008/0243028 A1 | 10/2008 | Howard et al. | |
| 2008/0243029 A1 | 10/2008 | Howard et al. | |
| 2008/0255427 A1* | 10/2008 | Satake et al. | 600/204 |
| 2008/0262616 A1 | 10/2008 | McKay | |
| 2008/0269566 A1* | 10/2008 | Measamer | 600/204 |
| 2008/0306608 A1 | 12/2008 | Nycz et al. | |
| 2009/0024224 A1 | 1/2009 | Chen et al. | |
| 2009/0047085 A1 | 2/2009 | Liao et al. | |
| 2009/0054906 A1 | 2/2009 | Walthall et al. | |
| 2009/0076556 A1 | 3/2009 | Mcgarity et al. | |
| 2009/0171359 A1 | 7/2009 | Sterrett | |
| 2009/0209962 A1 | 8/2009 | Jamali | |
| 2009/0275950 A1 | 11/2009 | Sterrett et al. | |
| 2009/0281550 A1 | 11/2009 | Keller | |
| 2009/0299371 A1 | 12/2009 | Steiner et al. | |
| 2009/0299372 A1 | 12/2009 | Steiner et al. | |
| 2009/0319051 A9 | 12/2009 | Nycz et al. | |
| 2010/0123325 A1 | 5/2010 | Maffeis | |
| 2010/0168750 A1 | 7/2010 | Sherman | |
| 2010/0249786 A1 | 9/2010 | Schmieding et al. | |
| 2010/0292704 A1 | 11/2010 | Stoffel et al. | |
| 2011/0009872 A1 | 1/2011 | Mistry et al. | |
| 2011/0046628 A1 | 2/2011 | Jamali | |
| 2011/0054408 A1 | 3/2011 | Wei et al. | |
| 2011/0137315 A1 | 6/2011 | Gil et al. | |
| 2011/0144648 A1 | 6/2011 | Gil et al. | |
| 2011/0208193 A1 | 8/2011 | Gil et al. | |
| 2012/0053588 A1 | 3/2012 | Lozier et al. | |
| 2012/0053642 A1 | 3/2012 | Lozier et al. | |

(56) References Cited

U.S. PATENT DOCUMENTS

| | | | | |
|---|---|---|---|---|
| 2012/0150030 A1* | 6/2012 | Reach et al. | ............... | 600/427 |
| 2013/0231745 A1 | 9/2013 | Lozier et al. | | |

FOREIGN PATENT DOCUMENTS

| | | | | |
|---|---|---|---|---|
| DE | 2830566 A | 1/1980 | | |
| DE | 2830566 A1 * | 1/1980 | ............ | A61B 17/16 |
| DE | 2933174 A1 | 4/1980 | | |
| DE | 4317448 A1 | 11/1994 | | |
| DE | 19503504 A1 | 3/1996 | | |
| DE | 19503504 A2 | 3/1996 | | |
| EP | 0307241 A2 | 3/1989 | | |
| EP | 0493698 A1 | 7/1992 | | |
| EP | 0508710 A1 | 10/1992 | | |
| EP | 0768332 A1 | 4/1997 | | |
| EP | 0815809 A2 | 1/1998 | | |
| EP | 0824893 A2 | 2/1998 | | |
| FR | 2700462 A1 | 7/1994 | | |
| GB | 2175506 A | 12/1986 | | |
| JP | 3178652 A | 2/1991 | | |
| JP | 4303450 A | 10/1992 | | |
| JP | 9122226 A | 5/1997 | | |
| JP | 10251492 A | 9/1998 | | |
| JP | 10513386 A | 12/1998 | | |
| WO | WO-9315694 A1 | 8/1993 | | |
| WO | WO-9426211 A1 | 11/1994 | | |
| WO | WO-9624302 A1 | 8/1996 | | |
| WO | WO-9624310 A1 | 8/1996 | | |
| WO | WO 96/27333 | 9/1996 | ............ | A61B 17/16 |
| WO | WO-9627333 A1 | 9/1996 | | |
| WO | WO-9725942 A1 | 7/1997 | | |
| WO | WO-9746665 A1 | 12/1997 | | |
| WO | WO98/34569 | 8/1998 | | |
| WO | WO-9834596 A2 | 8/1998 | | |
| WO | WO-9840027 A1 | 9/1998 | | |
| WO | WO-9856317 A1 | 12/1998 | | |
| WO | WO99/21497 | 5/1999 | | |
| WO | WO-0143667 A1 | 6/2001 | | |
| WO | WO-0224244 A2 | 3/2002 | | |
| WO | WO-2005023321 A2 | 3/2005 | | |
| WO | WO-2005094694 A2 | 10/2005 | | |
| WO | WO-2006026325 A2 | 3/2006 | | |
| WO | WO-2008/147692 A1 | 12/2008 | | |
| WO | WO-2010092100 A1 | 8/2010 | | |
| WO | WO-2011008968 A1 | 1/2011 | | |

OTHER PUBLICATIONS

Burba et al. (1992), "An arthroscopic biopsy procedure for obtaining osteochondral samples from the equine midcarpal joint," Journal of Investigative Surgery, vol. 5, pp. 343-359.

Convery, et al. (1991), "Fresh osteochondral allografting of the femoral condyle," Clinical Orthopaedics and Related Research, No. 273, pp. 139-145.

Gross (1992), "Use of fresh osteochondral allografts to replace traumatic joint defects," Allografts in Orthopaedic Practice, Ch. 5, pp. 67-82.

McDermott, et al. (1985), "Fresh small fragment osteochondral allografts," Clinical Orthopaedics and Related Research, No. 197, pp. 96-102.

Meyers, et al. (1989), "Resurfacing of the knee with fresh osteochondral allograft," The Journal of Bone and Joint Surgery, vol. 1A, No. 5, pp. 704-713.

Schachar et al. (1999), "Transplantation of cryopreserved osteochondral dowel allografts of focal articular defects in Ovine model," J. Orthop. Res., vol. 17, No. 6, pp. 909-919.

PCT International Search Report and Written Opinion dated Jun. 12, 2009, issued for PCT Application No. PCT/US2009/036661, filed Mar. 10, 2009.

Garrett, "Osteochondral Allografts for Reconstruction of Articular Defects of the Knee," AAOS Instructional Course Lectures, 1998, vol. 47, pp. 517-522.

Garrett, "Osteochondral Allografts," Ch. 34, pp. 355-358.

Hurtig et al., Vet. Surgery, "Osteochondral Dowel Transplantation for Repair of Focal Defects in the Knee: an Outcome Study Using an Ovine Model," 1998, vol. 27, pp. 5-16.

Macro Sensors, LVDT Basics, Technical Bulletin 0103 dated Jan. 31, 2003 (4 pages).

J.L. Ronsky et al., Precise Measurement of Cat Patellofemoral Joint Surface Geometry with Multistation Digital Photogrammetry, Journal of Biomechanical Engineering, vol. 121, pp. 196-205 (Apr. 1999).

Ian C. Clarke, Quantitative measurement of human articular surface topography in vitro by profile recorder and stereomicroscopy techniques, Journal of Microscopy, vol. 97, Pt. 3, Apr. 1973, pp. 309-314.

"U.S. Appl. No. 10/149,853, Non Final Office Action mailed Apr. 13, 2004", 7 pgs.

"U.S. Appl. No. 10/149,853, Notice of Allowance mailed Oct. 5, 2004", 7 pgs.

"U.S. Appl. No. 10/149,853, Preliminary Amendment mailed Oct. 17, 2002", 6 pgs.

"U.S. Appl. No. 10/149,853, Response filed Jul. 6, 2004 to Non Final Office Action mailed Apr. 13, 2004", 9 pgs.

"U.S. Appl. No. 11/705,575, Non Final Office Action mailed Mar. 15, 2005", 8 pgs.

"U.S. Appl. No. 11/705,575, Non Final Office Action mailed Sep. 15, 2011", 7 pgs.

"U.S. Appl. No. 11/705,575, Notice of Non-Compliant Amendment mailed Jan. 7, 2011", 3 pgs.

"U.S. Appl. No. 11/705,575, Notice of Non-Compliant Amendment mailed Oct. 29, 2010", 3 pgs.

"U.S. Appl. No. 11/705,575, Preliminary Amendment filed Feb. 12, 2007", 14 pgs.

"U.S. Appl. No. 11/705,575, Response filed Feb. 7, 2011 to Notice of Non-Compliant Amendment mailed Jan. 7, 2011", 22 pgs.

"U.S. Appl. No. 11/705,575, Response filed Sep. 15, 2010 to Non Final Office Action mailed Mar. 16, 2010", 13 pgs.

"U.S. Appl. No. 11/705,575, Response filed Nov. 29, 2010 to Notice of Non-Compliant Amendment mailed Oct. 29, 2010", 14 pgs.

"U.S. Appl. No. 11/705,575, Revised Preliminary Amendment filed Sep. 15, 2010 in Response to Office Action mailed Mar. 16, 2010", 11 pgs.

"U.S. Appl. No. 11/753,102, Advisory Action filed Dec. 10, 2010", 3 pgs.

"U.S. Appl. No. 11/753,102, Final Office Action mailed Aug. 3, 2010", 14 pgs.

"U.S. Appl. No. 11/753,102, Non Final Office Action mailed Jan. 4, 2010", 13 pgs.

"U.S. Appl. No. 11/753,102, Response filed May 4, 2010 to Non Final Office Action mailed Jan. 4, 2010", 13 pgs.

"U.S. Appl. No. 11/753,102, Response filed Nov. 23, 2009 to Restriction Requirement mailed Oct. 30, 2009", 12 pgs.

"U.S. Appl. No. 11/753,102, Response filed Dec. 3, 2010 to Final Office Action mailed Aug. 3, 2010", 15 pgs.

"U.S. Appl. No. 11/753,102, Restriction Requirement mailed Oct. 30, 2009", 9 pgs.

"U.S. Appl. No. 11/759,679, Final Office Action mailed Oct. 7, 2010", 17 pgs.

"U.S. Appl. No. 11/759,679, Non Final Office Action mailed Feb. 26, 2010", 14 pgs.

"U.S. Appl. No. 11/759,679, Response filed Jun. 28, 2009 to Non Final Office Action mailed Feb. 26, 2010", 13 pgs.

"U.S. Appl. No. 11/759,679, Response filed Oct. 30, 2009 to Restriction Requirement mailed Sep. 4, 2009", 3 pgs.

"U.S. Appl. No. 11/759,679, Restriction Requirement mailed Sep. 4, 2009", 6 pgs.

"U.S. Appl. No. 12/196,831, Advisory Action mailed Jan. 21, 2011", 3 pgs.

"U.S. Appl. No. 12/196,831, Final Office Action mailed Nov. 12, 2010", 9 pgs.

"U.S. Appl. No. 12/196,831, Non Final Office Action mailed Jul. 9, 2010", 7 pgs.

"U.S. Appl. No. 12/196,831, Non Final Office Action mailed Oct. 6, 2011", 8 pgs.

(56) References Cited

OTHER PUBLICATIONS

"U.S. Appl. No. 12/196,831, Response filed Jan. 10, 2011 to Final Office Action mailed Nov. 12, 2010", 10 pgs.
"U.S. Appl. No. 12/196,831, Response filed Jun. 21, 2010 to Restriction Requirement mailed Jun. 8, 2010", 8 pgs.
"U.S. Appl. No. 12/196,831, Response filed Oct. 7, 2010 to Non Final Office Action mailed Jul. 9, 2010", 11 pgs.
"U.S. Appl. No. 12/196,831, Restriction Requirement mailed Jun. 8, 2010", 7 pgs.
"International Application Serial No. PCT/US2008/063582, International Search Report mailed Oct. 9, 2008", 3 pgs.
"International Application Serial No. PCT/US2008/063582, Written Opinion mailed Oct. 9, 2008", 7 pgs.
"International Application Serial No. PCT/US2008/064653, International Search Report mailed Sep. 7, 2009", 3 pgs.
"International Application Serial No. PCT/US2008/064653, Written Opinion mailed Sep. 7, 2009", 8 pgs.
"U.S. Appl. No. 11/705,575, Notice of Allowance mailed May 15, 2012", 5 pgs.
"U.S. Appl. No. 12/196,831, Advisory Action mailed Jul. 5, 2012", 3 pgs.
"U.S. Appl. No. 12/196,831, Response filed Jun. 12, 2012 to Final Office Action mailed Apr. 12, 2012", 14 pgs.
"U.S. Appl. No. 12/873,030, Restriction Requirement mailed Jul. 10, 2012", 6 pgs.
"U.S. Appl. No. 12/873,049, Restriction Requirement mailed Jul. 10, 2012", 5 pgs.
"U.S. Appl. No. 12/873,030, Non Final Office Action mailed Oct. 30, 2012", 17 pgs.
"U.S. Appl. No. 12/873,030, Response filed Feb. 28, 2013 to Non Final Office Action mailed Oct. 30, 2012", 14 pgs.
"U.S. Appl. No. 12/873,049, Notice of Allowance mailed Nov. 14, 2012", 13 pgs.
"Australian Application Serial No. 200116857, Office Action mailed Feb. 13, 2004", 2 pgs.
"Canadian Application Serial No. 00979315.9, Office Action mailed Jan. 24, 2007", 3 pgs.
"Canadian Application Serial No. 00979315.9, Response filed Jul. 23, 2007 to Office Action mailed Jan. 24, 2007", 14 pgs.
"European Application Serial No. 04020622.9, European Search Report mailed Nov. 29, 2004", 6 pgs.
"European Application Serial No. 04020622.9, Office Action mailed Oct. 20, 2005", 3 pgs.
"European Application Serial No. 04020622.9, Response filed Apr. 13, 2006 to Office Action mailed Oct. 20, 2005", 12 pgs.
"International Application Serial No. PCT/CH00/00659, International Preliminary Examination Report mailed Mar. 20, 2002", 15 pgs.
"International Application Serial No. PCT/CH00/00659, International Search Report mailed Jan. 2, 2001", 8 pgs.
"International Application Serial No. PCT/US2008/063582, International Preliminary Report on Patentability mailed Nov. 24, 2009", 8 pgs.
"International Application Serial No. PCT/US2009/036661, International Preliminary Report on Patentability mailed Sep. 14, 2010", 9 pgs.
"Japanese Application Serial No. 2000-544609, Office Action mailed Jan. 5, 2010", 9 pgs.
"Japanese Application Serial No. 2000-544609, Office Action mailed Mar. 24, 2009", 8 pgs.
"Japanese Application Serial No. 2000-544609, Office Action mailed Aug. 5, 2008", 5 pgs.
"Japanese Application Serial No. 2000-544609, Office Action mailed Nov. 2, 2010", 7 pgs.
"Japanese Application Serial No. 2000-544609, Response filed Apr. 27, 2010 to Office Action mailed Jan. 24, 2010", 8 pgs.
"Japanese Application Serial No. 2000-544609, Response filed Jun. 11, 2009 to Office Action mailed Mar. 24, 2009", 14 pgs.
"Japanese Application Serial No. 2000-544609, Response filed Oct. 28, 2008 to Office Action mailed Aug. 5, 2008", 14 pgs.
Albee, Fred H, "Bone Surgery With Machine Tools", Scientific American vol. 154.4, (Apr. 1936), 178-181.
U.S. Appl. No. 13/855,157, filed Apr. 2, 2013, Osteochondral Graft Delivery Device and Uses Thereof.
"U.S. Appl. No. 10/149,853, Preliminary Amendment filed Sep. 14, 2012", 7 pgs.
"U.S. Appl. No. 11/753,102, Non Final Office Action mailed Feb. 26, 2014", 9 pgs.
"U.S. Appl. No. 12/196,831, Examiner Interview Summary mailed Nov. 25, 2013", 3 pgs.
"U.S. Appl. No. 12/196,831, Final Office Action mailed Jan. 30, 2014", 19 pgs.
"U.S. Appl. No. 12/196,831, Non Final Office Action mailed Oct. 3, 2013", 21 pgs.
"U.S. Appl. No. 12/196,831, Response filed Nov. 27, 2013 to Non-Final Office Action dated Oct. 3, 2013", 13 pgs.
"U.S. Appl. No. 12/873,030, Advisory Action mailed Oct. 16, 2013", 3 pgs.
"U.S. Appl. No. 12/873,030, Final Office Action mailed Aug. 1, 2013", 14 pgs.
"U.S. Appl. No. 12/873,030, Non Final Office Action mailed Nov. 6, 2013", 11 pgs.
"U.S. Appl. No. 12/873,030, Response filed Oct. 1, 2013 to Final Office Action mailed Aug. 1, 2013", 15 pgs.
"U.S. Appl. No. 12/873,049, Notice of Allowance mailed Mar. 25, 2013", 9 pgs.
"U.S. Appl. No. 13/619,022, Non Final Office Action mailed May 8, 2013", 6 pgs.
"U.S. Appl. No. 13/855,157, Non Final Office Action mailed Oct. 10, 2013", 15 pgs.
"U.S. Appl. No. 13/855,157, Notice of Allowance mailed Feb. 11, 2014", 10 pgs.
"U.S. Appl. No. 13/855,157, Preliminary Amendment filed Apr. 5, 2013", 7 pgs.
"U.S. Appl. No. 13/855,157, Response filed Jan. 10, 2014 to Non-Final Office Action dated Oct. 10, 2013", 8 pgs.
"International Application Serial No. PCT/US2008/064653, International Preliminary Report on Patentability mailed", 9 pgs.
"U.S. Appl. No. 11/705,575, Response filed Dec. 15, 2011 to Non Final Office Action mailed Sep. 15, 2011", 14 pgs.
"U.S. Appl. No. 12/196,831, Examiner Interview Summary mailed Feb. 6, 2012", 18 pgs.
"U.S. Appl. No. 12/196,831, Final Office Action mailed Apr. 12, 2012", 17 pgs.
"U.S. Appl. No. 12/196,831, Response filed Feb. 1, 2012 to Non Final Office Action mailed Oct. 6, 2011", 15 pgs.
"U.S. Appl. No. 12/196,831, Response filed Sep. 12, 2012 to Advisory Action mailed Jul. 5, 2012", 16 pgs.
"U.S. Appl. No. 12/873,030, Response filed Jul. 27, 2012 to Restriction Requirement mailed Jul. 10, 2012", 7 pgs.
"U.S. Appl. No. 12/873,049, Response filed Jul. 27, 2012 to Restriction Requirement mailed Jul. 10, 2012", 8 pgs.
"International Application Serial No. PCT/US2009/036661, International Search Report mailed Jun. 12, 2009", 4 pgs.
"International Application Serial No. PCT/US2009/036661, Written Opinion mailed Jun. 12, 2009", 8 pgs.
Bobic, V, "Arthroscopic osteochondral autograft transplantation in anterior cruciate ligament reconstruction: a preliminary clinical study", Knee Surg, Sport Traumatol, Arthroscopy 3, (1996), 262-264.
Convery, F.R., et al., "The Repair of Large Osteochondral Defects", An Experimental Study in Horses, Clin. Orthrop. 82., (1972), 253-262.
Ehalt, W, "Bisherige Erfahrungen mit dem plastischen Ersatz von Gelenkknorpel aus der Knochenbank", Verh. Dtsch. Orthop. Ges. 43, (1955), 107-109.
Ehalt, W., et al., "Gelenkknorpel-Plastik", Langenbecks Arch. Kiln. Chir. 299, (1962), 768-774.
Ehalt, Walther M, "Grafting of joint-cartilage Bone-Blocks from the bank", VI. Congr. Soc. Internat. Chir. Orthop. Traumatol. S., (1954), 419-421.

(56) References Cited

OTHER PUBLICATIONS

Garrett, John C, "Treatment of Osteochondral Defects of the Distal Femur with Fresh Osteochondral Allografts: A Preliminary Report", Arthroscopy: The Journal of Arthroscopic and Related Surgery 2(4), (1986), 222-226.

Guhl, James F, "Chapter 21: The Impact of Arthroscopy on Osteochondritis Dissecans", Operative Arthroscopy, (1991), 297-317.

Hangody, L, et al., "Autogenous osteochondral grafting in the knees of German Shepherd dogs: Radiographic and histological analysis", Hungarian Review of Sports Medicine 35, (1994), 117-123.

Hangody, L, et al., "Treatment of localized chondral and osteochondral defects in the knee by a new autogenous osteochondral grafting tenique", Hungarian Review of Sports Medicine 35, (1994), 241-246.

Hangody, Laszlo, "Arthroscopic autogeous osteochondral mosaicplasty for the treatment of femoral condylar articular defects: A preliminary report", Knee Surg, Sports Traumatol, Arthrosc 5, (1997), 262-267.

Hangody, Laszlo, et al., "Artoszkopos autolog osteochondralis mozaikplastica (Arthroscopic autogenous osteochondral mosaicplasty)", Hungarian Journal of Traumatology and Orthopaedics 39, (1996), 49-54.

Hangody, Laszlo, "Autologous osteochondral mosaic-like graft technique for replacing weight bearing cartilage defects", 7th Congres of ESSTKSA, Abstract Only, (1996), 3 pgs.

Hangody, Laszlo, et al., "Autologous Osteochondral Mosaic-Plasty", Review of Osteology 3, (1996), 70-73.

Hangody, Laszlo, "Chapter 13: Autogenous Osteochondral Mosaicplasty for the Treatment of Focal Chondral and Osteochondral Defects of the Femoral Condyles", Knieinstabilitat und Knorpelschaden, (1998), 97-106.

Hangody, Laszlo, "Mosaic-plasty in Clinical Practice", Review of Osteology 4, (1996), 32-36.

Hangody, Laszlo, et al., "Mosaicplasty for the Treatment of Articular Cartilage Defects: Application in Clinical Practice", Orthopedics 21(2), (1998), 751-756.

Hangody, Laszlo, et al., "Mosaicplasty for the treatment of osteochondritis dissecans of the knee", [Online]. Retrieved from the Internet: <URL: http://www.egydoc.com/Sites/Arthroclub/AC__Files/Articles/article39.pdf>, (Accessed Nov. 8, 2005), 9 pgs.

Hangody, Laszlo, et al., "New Method in Treatment of Sever Local Cartilage Damage in the Knee Joint (Eine neue Methode in der Behandlung von schweren, lokalen Knorpelschaden im Kniegelenk", Osteosynthese International 5, (1997), 316-321.

Hangody, Laszlo, et al., "Osteochondral Plugs: Autogenous Osteochondral Mosaicplasty for the Treatment of Focal Chondral and Osteochondral Articular Defects", Operative Techniques in Orthopaedics 7(4), (1997), 312-322.

Hangody, Laszlo, et al., "Súlyos, körülírt térdízületi porckárosodás sebészi kezelésének új lehetósége (New alternative in the treatment of sever, localized cartilage damages in the knee joint)", Hungarian Journal of Traumatology and Orthopaedics 37, (1994), 237-242.

Hangody, Laszlo, et al., "Treatment of Osteochondritis Dissecans of the Talus: Use of Mosaicplasty Technique—A Preliminary Report", Foot and Ankle International 18(10), (1997), 628-634.

Lindholm, Sam, et al., "Reconstruction of the Articular Surface by Transfixation of an Osteochondral Fragment of the Femoral Condyle Using a Bone Transplant", Scandinavian Journal of Rheumatology Supplement 44, (1982), 5-13.

Muller, W, "Osteochondrosis Dissecans", Progress in Orthopaedic Surgery vol. 3, (1978), 135-142.

Woods, T, "Effectiveness of three extraction techniques in the development of a decellularized bone-anterior cruciate ligament-bone graft", Biomaterials, Elsevier Science Publishers BV., Barking, GB, vol. 26, No. 35, (Dec. 1, 2005), 7339-7349.

Yamashita, et al., "The Transplantation of an Autogeneic Osteochondral Fragment for Osteochondritis Dissecans of the Knee", Clinical Orthopaedics and Related Research, No. 201, (1985), 43-50.

\* cited by examiner

INSTRUMENTS AND METHODS USED WHEN REPAIRING A DEFECT ON A TISSUE SURFACE

TECHNICAL FIELD

This invention relates to medical devices and methods, and more particularly to medical instruments and methods used when repairing defects on a tissue surface such as bone or cartilage.

BACKGROUND

Medical implants are often delivered to anatomical sites within a patient's body to treat focal defects. For example, damaged cartilage or bone within a patient's body may include a cavity or void formed by trauma, disease, or surgery. The cavity or void may leave the bone prone to further injury or damage, especially when the cavity or void is formed in a weight-bearing joint such as the knee. To treat such a defect, the affected tissue may be drilled out or otherwise prepared to receive an implant designed to promote tissue formation. The implant may comprise healthy cartilage and/or bone cut from other locations on the patient's body, tissue(s) harvested from a donor, and/or synthetic material(s) such as porous ceramics or metals, biocompatible polymers, or combinations thereof.

Preparing a defect to receive an implant can be a challenging task. Ideally, the defect should be prepared to a size and shape corresponding to that of the implant. This includes not only the dimensions of the prepared cavity, but also its orientation relative to the surrounding tissue surface. For example, bone plugs and similar implants are often cut from bone at angles substantially perpendicular to the surface of the bone. If such a bone plug is delivered into a cavity drilled at an angle to the surrounding surface, the end of the bone plug may not properly correspond to the surrounding surface. Portions of the bone plug may extend out of the cavity (i.e., be "proud") so as to create an undesirable protrusion relative to the surrounding surface. Alternatively or additionally, portions of the bone plug may be recessed relative to the surrounding surface such that a defect in the bone remains.

Conventional techniques for properly orienting an instrument, such as a cutting tool, relative to a tissue surface rely solely upon visual and/or tactile feedback. After placing the cutting tool in contact with the tissue surface, a surgeon may simply change the angle of the cutting tool until she believes it looks or feels perpendicular to the tissue surface. The surgeon then attempts to maintain this orientation throughout the procedure. As can be appreciated, such techniques involve a great degree of approximation and may still result in cavities with undesirable orientations. Moreover, oftentimes the surgeon cannot directly view the tissue surface (e.g., because the procedure is performed arthroscopically). Attempting to properly orient a cutting tool while looking through an arthroscope can be even more challenging due to the magnification of the arthroscope.

As a result, various devices have been developed to facilitate preparing a defect to receive an implant. For example, U.S. Pat. No. 5,885,293 to McDevitt discloses a tool for cutting bone surfaces at perpendicular angles. The tool includes a cylindrical bone cutter, a cylindrical housing mounted on a handle of the bone cutter, a probe that slides within an inner bore of the bone cutter and the housing, and a ring on the exterior of the housing connected to the probe by a pin extending through the housing. The probe is biased to normally extend beyond the end of the bone cutter. When the bone cutter is placed against a bone surface, the probe is displaced into the inner bore. This displacement causes the ring to slide along the exterior of the housing, which includes indicia so that the displacement of the probe may be viewed. A surgeon manipulates the tool until maximum displacement is achieved, which, according to McDevitt, which generally corresponds to perpendicular alignment.

Although McDevitt offers an alternative to conventional techniques for orienting a tool relative to a bone surface, there remains room for improvement. The maximum displacement of a single probe may not always provide a reliable indication of perpendicular alignment. This is particularly true when using the tool disclosed in McDevitt to determine the proper orientation for repairing a defect on a tissue surface. For example, because the probe is a cylindrical element that slides along the center axis of the bone cutter, the probe is likely to contact the cavity defining the defect when the bone cutter is brought into contact with the bone surface. The maximum displacement of the probe found after manipulating the bone cutter may not necessarily reflect perpendicular alignment due to the differences (e.g. irregularities) between the defect and the profile of the surrounding surface.

Accordingly, an improved instrument to determine the proper orientation for repairing a defect on a tissue surface would be highly desirable.

SUMMARY

Medical instruments and methods used when repairing defects on a tissue surface are described below. The instruments and methods are particularly suited to facilitate repairing defects on irregular surfaces (e.g., multi-radii, articular, and similar surfaces), although the instruments and methods may also be used in connection with other tissue surfaces. Additionally, the instruments may serve a variety purposes. The instruments described below may be used, for example, as an implant delivery device, punch, drill, guide tube, tamp, sleeve, obturator, cutting device, or some combination thereof.

In one embodiment, an instrument for determining the proper orientation for repairing a defect site on a tissue surface generally comprises a shaft, a plurality of probes operatively coupled to the shaft, and at least one indicator operatively coupled to the plurality of probes. The shaft includes a first end configured to contact the tissue surface and a second end opposite the first end. Each of the probes is moveable relative to the shaft and configured to extend beyond the first end. Because the indicator is configured to display the displacements of the probes relative to the first end, the displacements of the probes may be compared. There may be a single indicator or a plurality of indicators corresponding to the plurality of probes.

In another embodiment, the instrument is provided as part of an assembly that further includes a defect preparation tool. The shaft in such an embodiment may be a cannula defined by an outer wall surrounding a central bore. The defect preparation tool, which may be inserted through the central bore, is configured to prepare the defect site for receiving an implant. Alternatively or additionally, the implant may be provided as part of the assembly. The implant is configured to be received within the central bore of the shaft and is delivered to the defect site through the central bore.

One method of using the type of instrument described above generally comprises positioning the instrument proximate to a patient's body and contacting the tissue surface with the first end of the shaft and the plurality of probes. The displacement of each probe relative to the first end is transmitted to the at least one indicator. A user then determines the angle of the shaft relative to the tissue surface based on displacement information displayed or otherwise communicated by the at least one indicator. If necessary, the user adjusts the angle of the shaft relative to the tissue surface until a desired orientation is achieved.

When there is a plurality of indicators each configured to display the displacement information of one of the probes, the angle of the shaft may be determined by viewing the displacement information of each probe. After comparing the displacement information of at least two of the probes, the angle of the shaft may be adjusted until the displacements of the at least two probes are substantially equal.

In another embodiment, the method may further comprise substantially maintaining the shaft at a desired angle (e.g., 90°) relative to the tissue surface. The shaft may be a cannula defined by an outer wall surrounding a central bore. After inserting a defect preparation tool through the central bore, the defect site on the tissue surface is prepared to receive an implant. To this end, the defect preparation tool may be subsequently removed from the shaft so that the implant may be inserted into the central bore and delivered to the defect site through the shaft.

DETAILED DESCRIPTION

Figure 1:
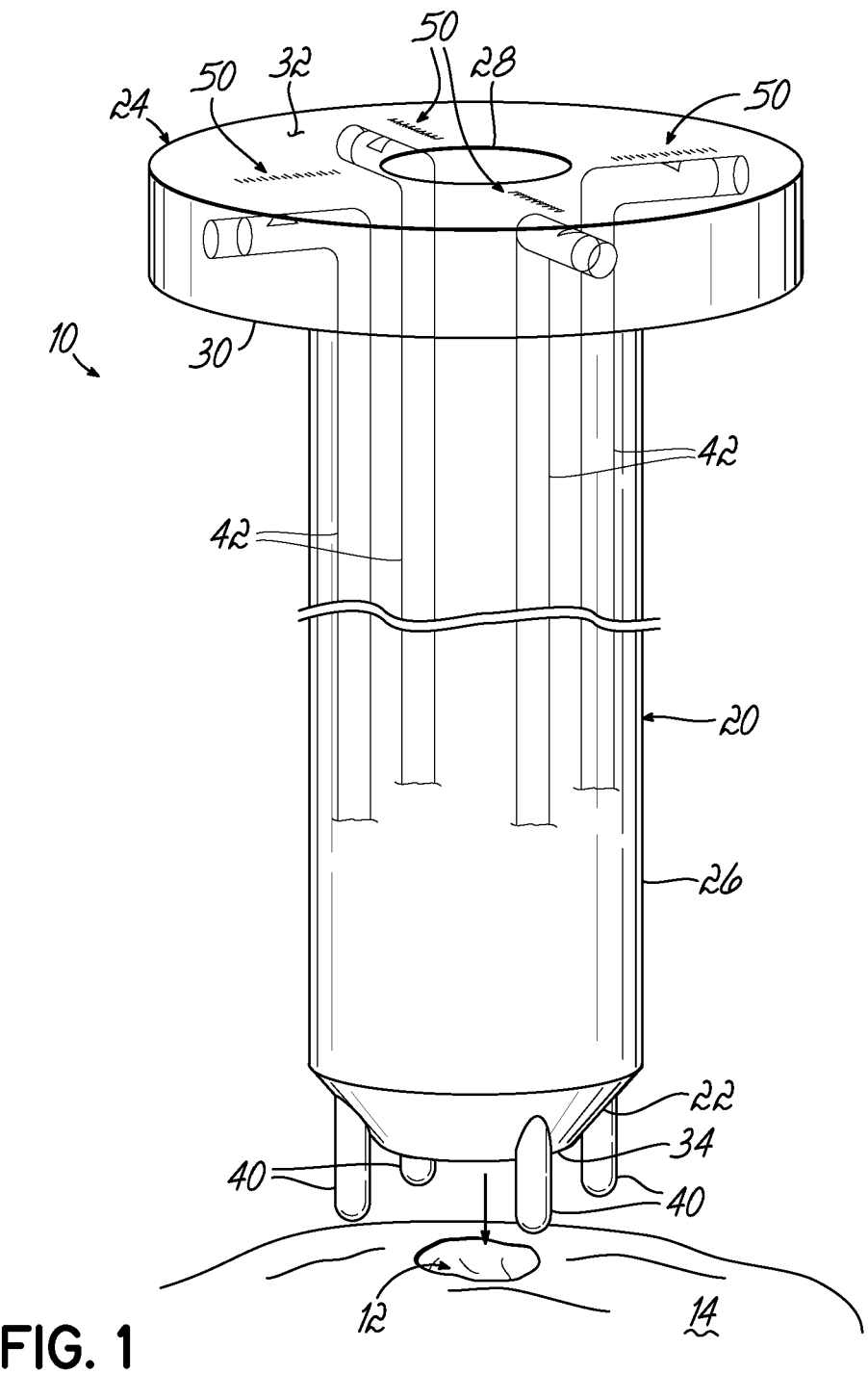
FIG. 1 is a perspective view showing one embodiment of an instrument for determining the proper orientation for repairing a defect site on a tissue surface.

FIG. 1 shows one embodiment of an instrument 10 for determining the proper orientation for repairing a defect site 12 on a tissue surface 14. The tissue surface 14 may be a bone surface, a cartilage surface, a skin surface, a dental surface, or any other surface having a defect that requires treatment. For example, the defect site 12 may be located in the articular cartilage covering the condyles (not shown) at the distal end of the femur. In such situations, the instrument 10 is particularly advantageous for establishing an angle substantially perpendicular to the tissue surface 14, as will be described in greater detail below.

The instrument 10 includes a shaft 20 having a first end 22 configured to contact the tissue surface 14 and a second end 24 opposite the first end 22. In the illustrative embodiment shown, the shaft 20 is a cannula defined by an outer wall 26 surrounding a central bore 28. The first end 22, which may be beveled or flat, has a first diameter and the second end 24 has a second diameter larger than the first diameter. As a result, the second end 24 defines a flange portion 30. The flange portion 30 terminates in an upper surface 32 and the first end 22 terminates in a lower surface 34. Although the entire shaft 20 is shown as being transparent (for reasons discussed below), in other embodiments the shaft 20 may only be transparent in select areas or not transparent at all.

A plurality of probes 40 are operatively coupled to the shaft 20 and configured to extend beyond the first end 22. For example, the probes 40 may be partially received in a plurality of channels 42 extending into the outer wall 26 from the lower surface 34. The number of probes 40 and their spacing relative to each other may vary. FIG. 1 illustrates four of the probes 40 equally spaced about the periphery of the shaft 20. Because the shaft 20 is substantially cylindrical, each of the probes 40 are spaced approximately 90° apart from adjacent probes 40. In other embodiments, the instrument 10 may only include two probes 40 spaced approximately 180° apart. Equally spacing an even number of probes 40 apart from each other has particular advantages that will be described in greater detail below. However, in alternative embodiments, an odd number of probes 40 may be spaced about the periphery of the shaft 20.

The probes 40 are movable relative to the shaft 20, and the displacement of each probe 40 relative to the first end 22 is communicated to at least one indicator 50. FIG. 1 shows a plurality of indicators 50 corresponding to the number of probes 40. However, those skilled in the art will appreciate that the displacements of the probes 40 may alternatively be communicated to a single indicator (not shown) or to a different number of indicators. Any type of indicator configured to communicate the displacements of the probes 40 to a practitioner utilizing the instrument 10 may be used.

Figure 2:
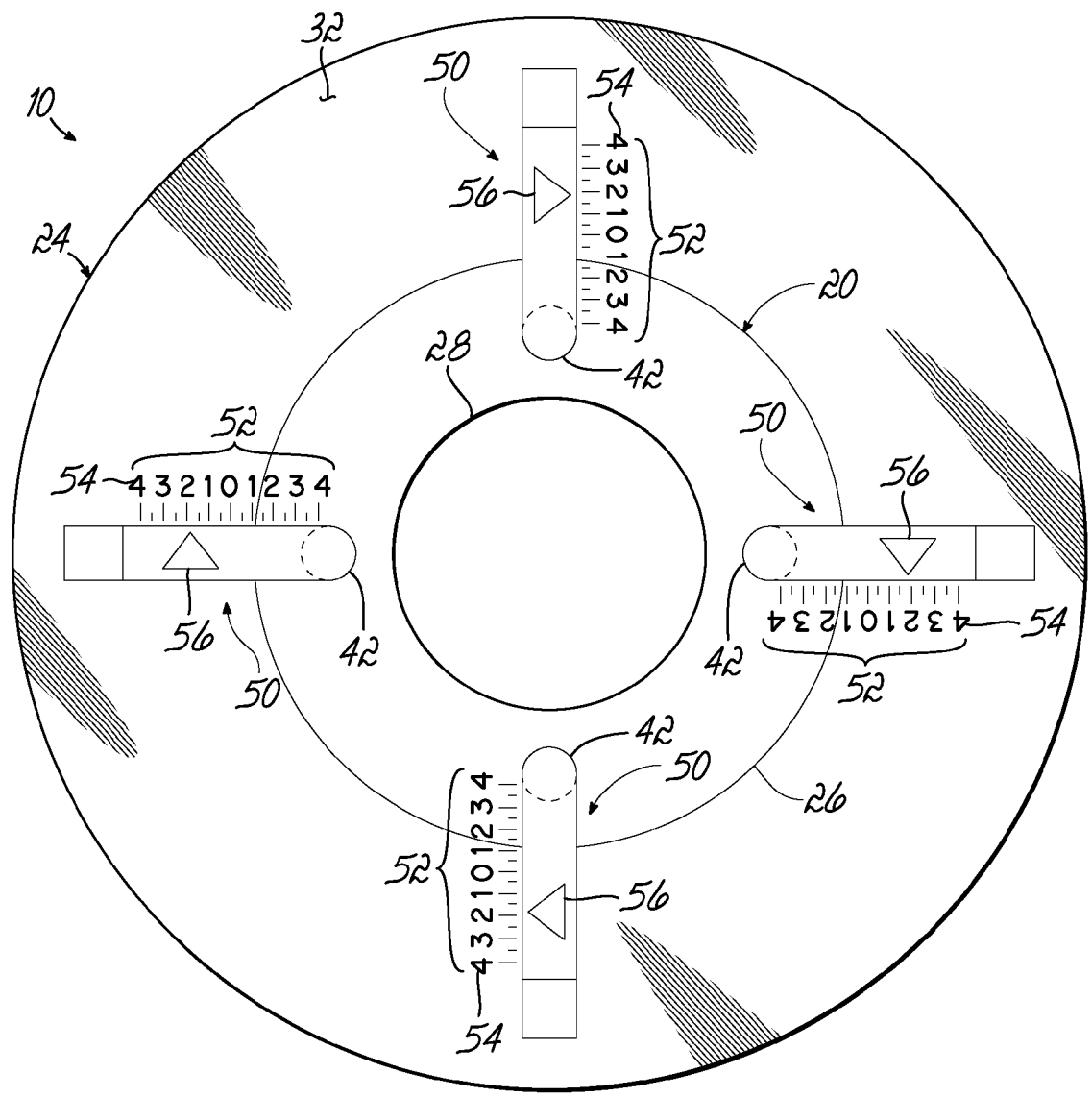
FIG. 2 is top view of the instrument shown in FIG. 1.

For example, as shown in FIG. 2, the indicators 50 may each comprise a displacement scale 52 provided on the upper surface 32. Each displacement scale 52 is marked with indicia 54 corresponding to the distance of the distal end of one of the probes 40 (FIG. 1) relative to the first end 22. A marking element 56 moves along the indicia 54 when the associated probe 40 moves relative to the first end 22. The transparency of the shaft 20, and the upper surface 32 in particular, allows a practitioner to view the displacement information. The portions of the upper surface above the marking elements 56 may be the only transparent portions of the shaft 20 in some embodiments. Additionally, rather than providing visual indication of the displacements, the indicators 50 may alternatively be configured to provide tactile and/or audible feedback to communicate the displacements to a practitioner. The manner in which the displacements are transmitted to the indicators 50 may vary. Several representative examples are described below, with like reference numbers being used to refer to like structure throughout the various embodiments.

Figure 3A:
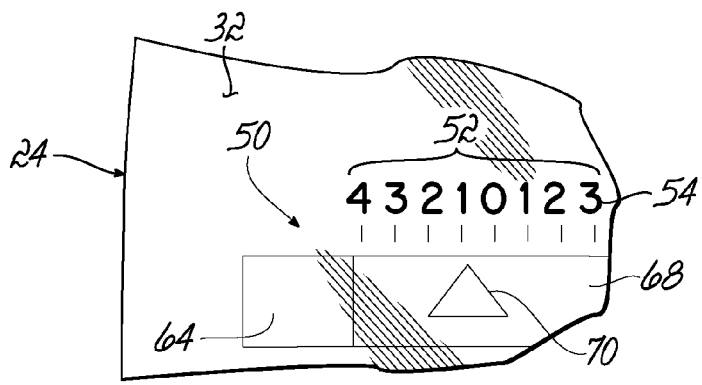
FIG. 3A is a top view taken along line 3A-3A showing a portion of the instrument of FIG. 3.
Figure 3:
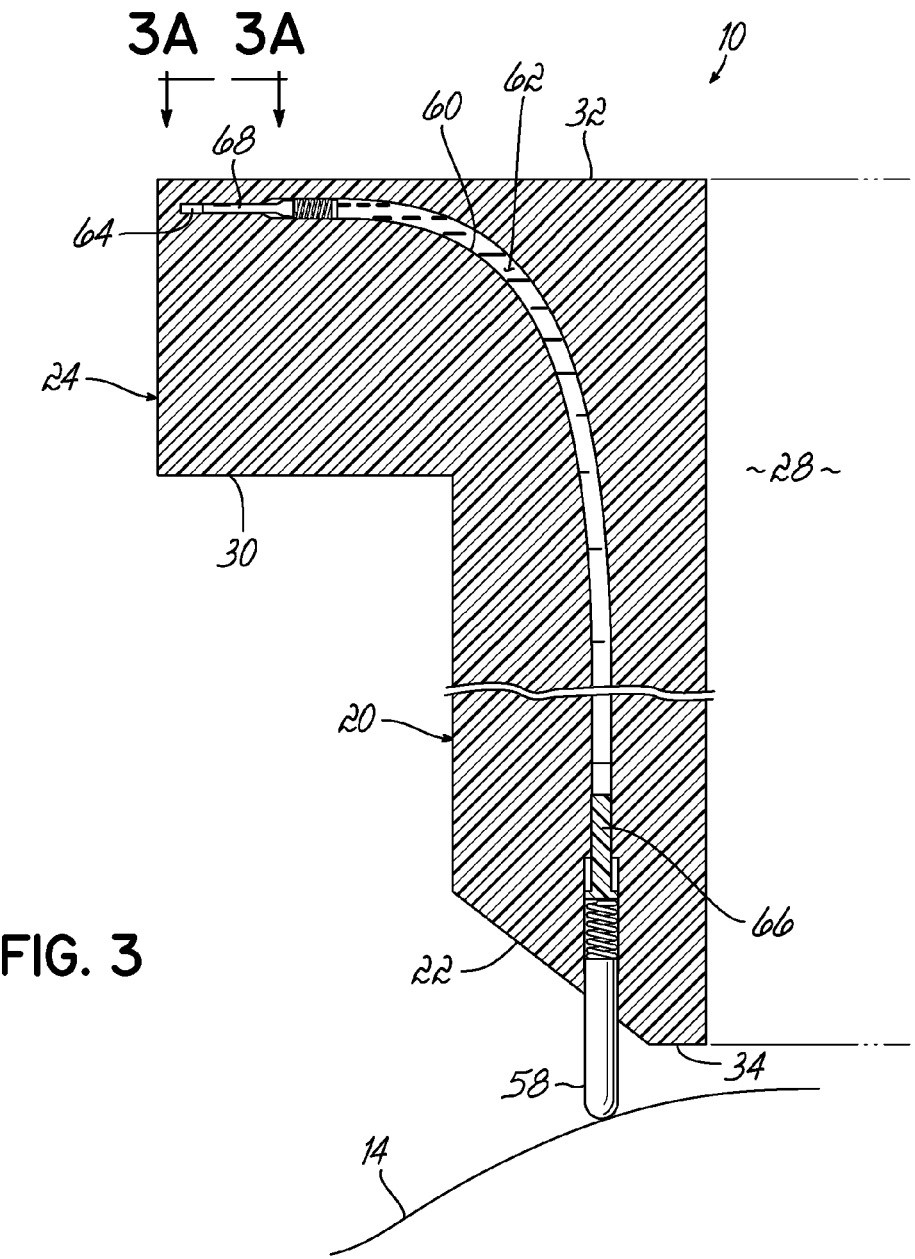
FIG. 3 is a cross-sectional view of a portion of an instrument according to an embodiment in which the displacement of a probe is hydraulically communicated to an indicator.

First, FIG. 3 is a cross-section of a portion of the shaft 20 illustrating a probe 58 and channel 60 in further detail. The probe 58 in this embodiment is operatively coupled to the indicator 50 (FIG. 3A) by fluid 62 (e.g., liquid and/or gas) within the channel 60 so that the displacement of the probe 58 is hydraulically and/or pneumatically communicated to the indicator 50. More specifically, the channel 60 extends upward from the first end 22 before curving outwardly toward the periphery of the shaft 20 within the flange portion 30. An upper portion 64 of the channel 60 may be visible through the upper surface 32.

The fluid 62 is maintained within the channel 60 by first and second plunger elements 66, 68 that seal, engage, and move within the channel 60. The first plunger element 66 is positioned proximate to the first end 22 and coupled to the probe 58. As a result, the probe 58 displaces the first plunger element 66 within the channel 60 when moving relative to the first end 22. The fluid 62 within the channel 60 communicates this displacement to the second plunger element 68, which is positioned in the upper portion 64 of the channel 60. As shown in FIG. 3A, the second plunger element 68 may be provided with a scribe 70 that can be seen from the upper surface 32 so as to serve as the marking element 56 (FIG. 2) of the indicator 50. The second plunger element 68 moves the scribe 70 along the displacement scale 52 in response to changes in fluid pressure and displacement created by the movement of the first plunger element 66 within the channel 60.

Figure 4A:
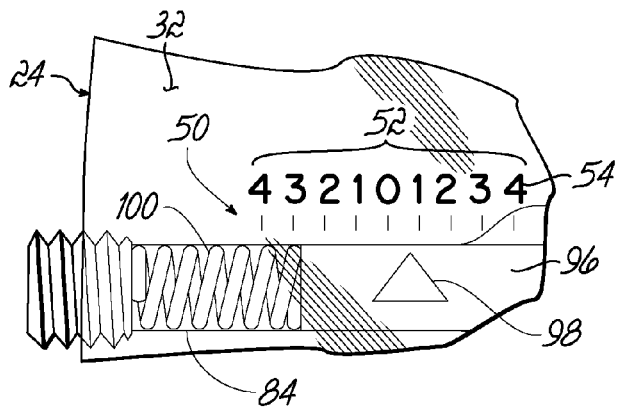
FIG. 4A is a top view taken along line 4A-4A showing a portion of the instrument of FIG. 4.
Figure 4:
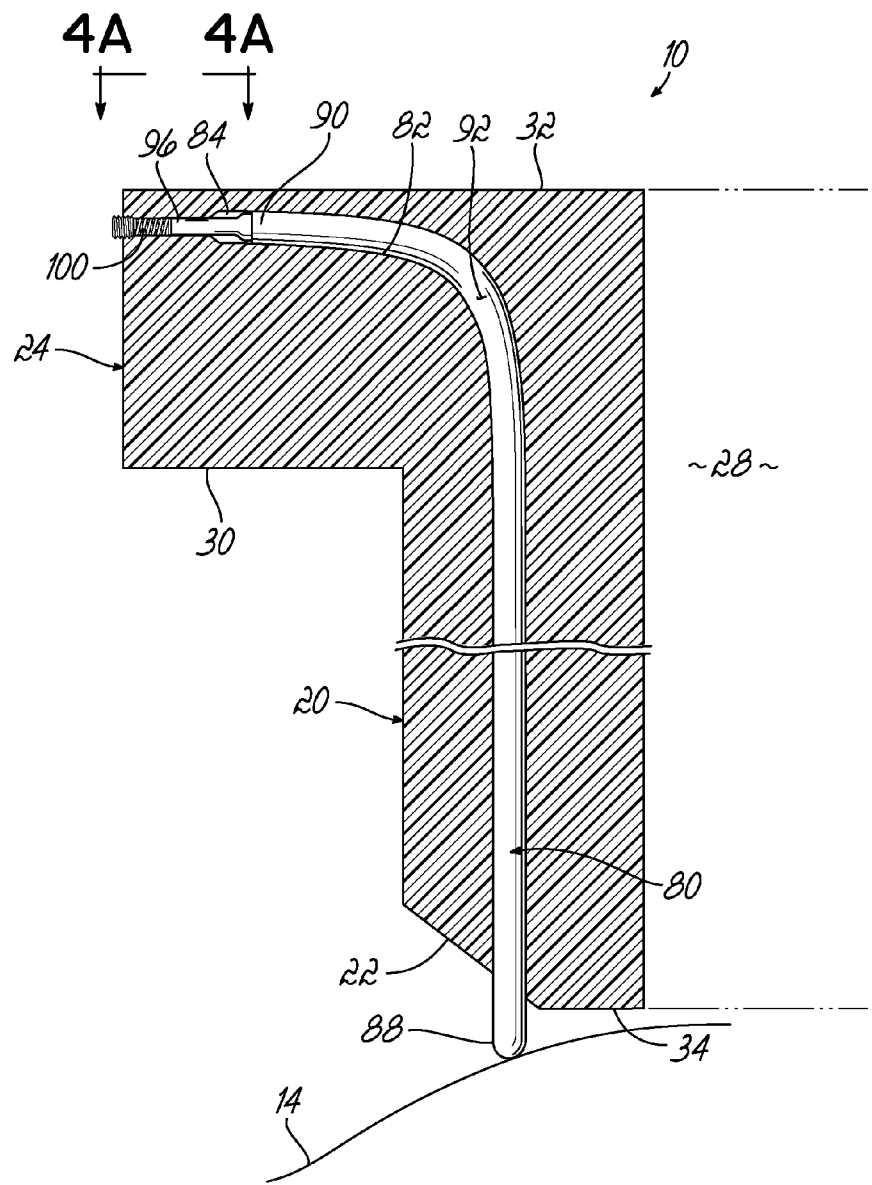
FIG. 4 is a cross-sectional view similar to FIG. 3, but showing a portion of an instrument according to an embodiment in which the displacement of a probe is mechanically communicated to an indicator.

With reference to FIG. 4, the displacement of a probe 80 may instead be mechanically communicated to the indicator 50. Such an embodiment may still include a channel 82 extending from the first end 22 of the shaft 20 and curving into the flange portion 30. The channel 82 may also include an upper portion 84 visible through the upper surface 32. However, the probe 80 may comprise an elongated element occupying a substantial portion of the channel 82. The probe 80 has a tip portion 88 configured to contact the tissue surface 14 and an end portion 90 extending into the upper portion 84 of the channel 82.

The tip portion 88, end portion 90, and a middle portion 92 therebetween may comprise the same or different materials. In one embodiment, the tip portion 88 comprises a first material and the middle portion 92 and/or end portion 90 comprises a second material that is less rigid than the first material. For example, the first material may be steel or titanium and the second material may be nitinol. It will be appreciated that the first material is selected to provide the tip portion 88 with sufficient rigidity so as to be effectively displaced within the channel 82 upon contact with the tissue surface 14. The second material is selected to provide the middle portion 92 and/or end portion 90 with sufficient flexibility to translate through the channel 82 despite its curvature. Advantageously, the end portion 90 and middle portion 92 are captured within the channel 82 to prevent separation of the probe 80 from the shaft 20 and to prevent interference with the movement of the probe 80.

The end portion 90 of the probe 80 is configured to communicate the displacement of the tip portion 88 to the indicator 50. More specifically, the end portion 90 may include a plunger element 96 configured to slide within the upper portion 84 of the channel 82. Although FIG. 4A illustrates the plunger element 96 including a scribe 98 that serves as the marking element 56 (FIG. 2), the scribe 98 may alternatively be provided on a contiguous segment of the probe 80 so as to eliminate the need for the plunger element 96. A spring 100 biases the end portion 90 within the channel 82 so that the tip portion 88 normally extends an initial distance beyond the first end 22. When the tip portion 88 is displaced into the channel 82, the probe 80 moves relative to the shaft 20 and causes the scribe 98 to move along the displacement scale 52.

Figure 5A:
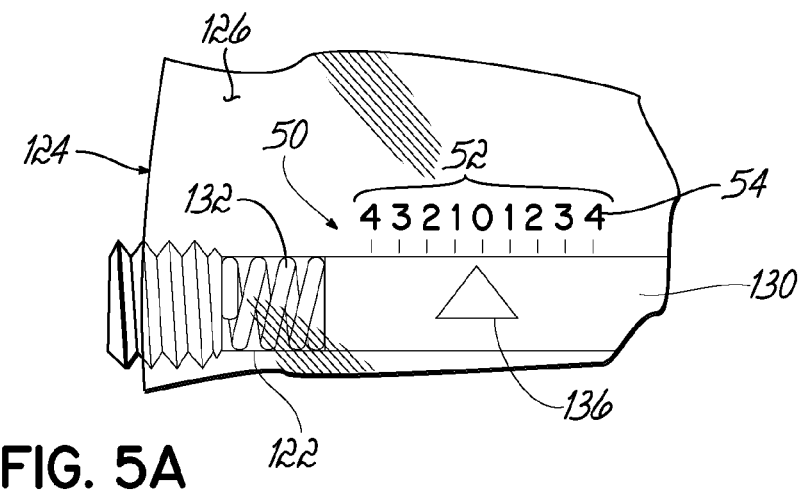
FIG. 5A is a top view taken along line 5A-5A showing a portion of the instrument of FIG. 5.
Figure 5:
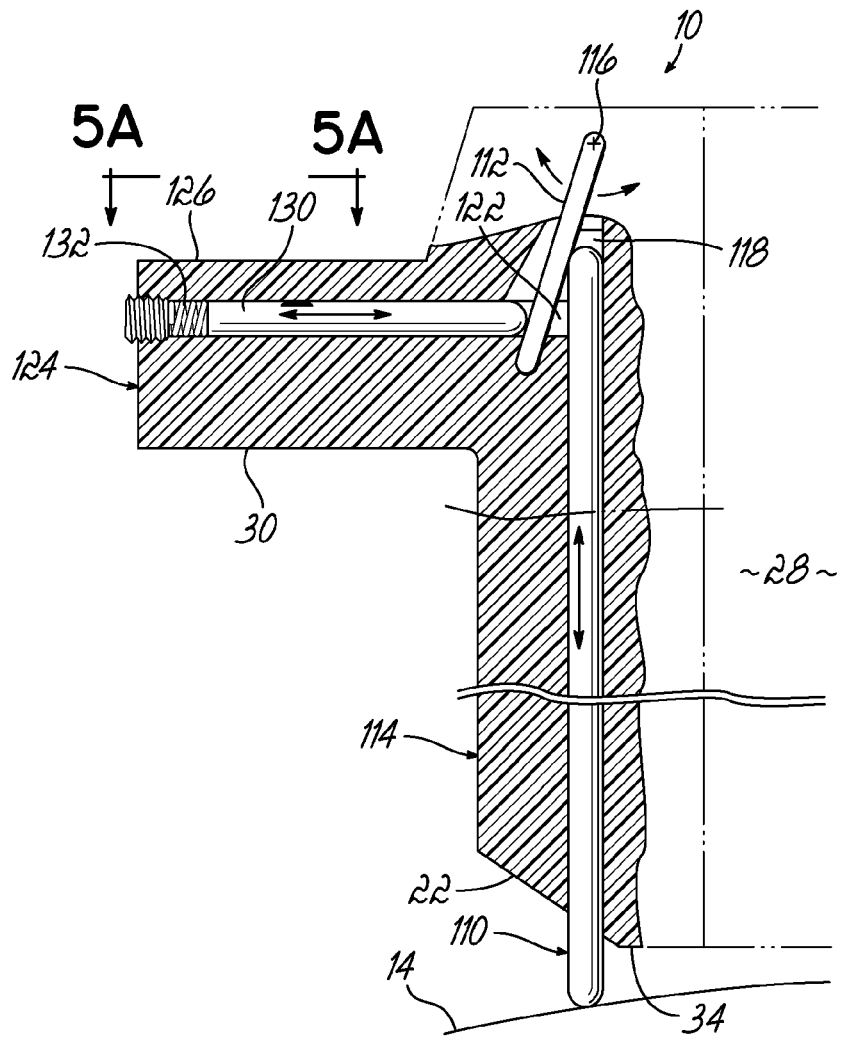
FIG. 5 is a cross-sectional view similar to FIG. 3, but showing a portion of an instrument according to another embodiment in which the displacement of the probe is mechanically communicated to the indicator.

FIG. 5 illustrates an alternative embodiment in which the displacement of a probe 110 relative to the first end 22 is amplified as it is mechanically communicated to the indicator 50. In the embodiment shown, the amplification is accomplished by providing a lever 112 within a shaft 114. The lever 112 is coupled to the shaft 114 at a pivotal connection 116 above a first channel 118, which extends upwardly from the lower surface 34 in a generally vertical direction. The probe 110 is a first elongated element configured to slide within the first channel 118. When the probe 110 contacts the lever 112, the lever 112 is rotated about the pivotal connection 116.

The shaft 114 further includes a second channel 122 that extends through a flange portion 124 in a generally horizontal direction. The second channel 122 may be visible through an upper surface 126, much like the upper portions 64 (FIG. 3) and 84 (FIG. 4), and the indicator 50 may once again be a displacement scale 52 provided on the upper surface 126. A second elongated element 130 is received in the second channel 122 and may be biased toward the first channel 118 by a spring 132. The second elongated element 130 contacts the lever 112 on an opposite side and spaced apart from the probe 110. Thus, when the probe 110 is displaced within the first channel 118 to rotate the lever 112, the lever 112 will displace the second elongated element 130 outwardly toward the periphery of the shaft 114. The displacement of the second elongated element 130 relative to that of the probe 110 will depend upon the mechanical advantage provided by the lever 112. This displacement may be viewed and analyzed by providing a scribe 136 (FIG. 5A) on the second elongated element 130 that moves along the displacement scale 52. As with the previous embodiment, the components associated with the probe 110 (e.g., the lever 112, the second elongated element 130) and portions of the probe 110 itself are captured within the shaft 114 to prevent separation from the shaft 114 and interference with their operation.

Figure 6:
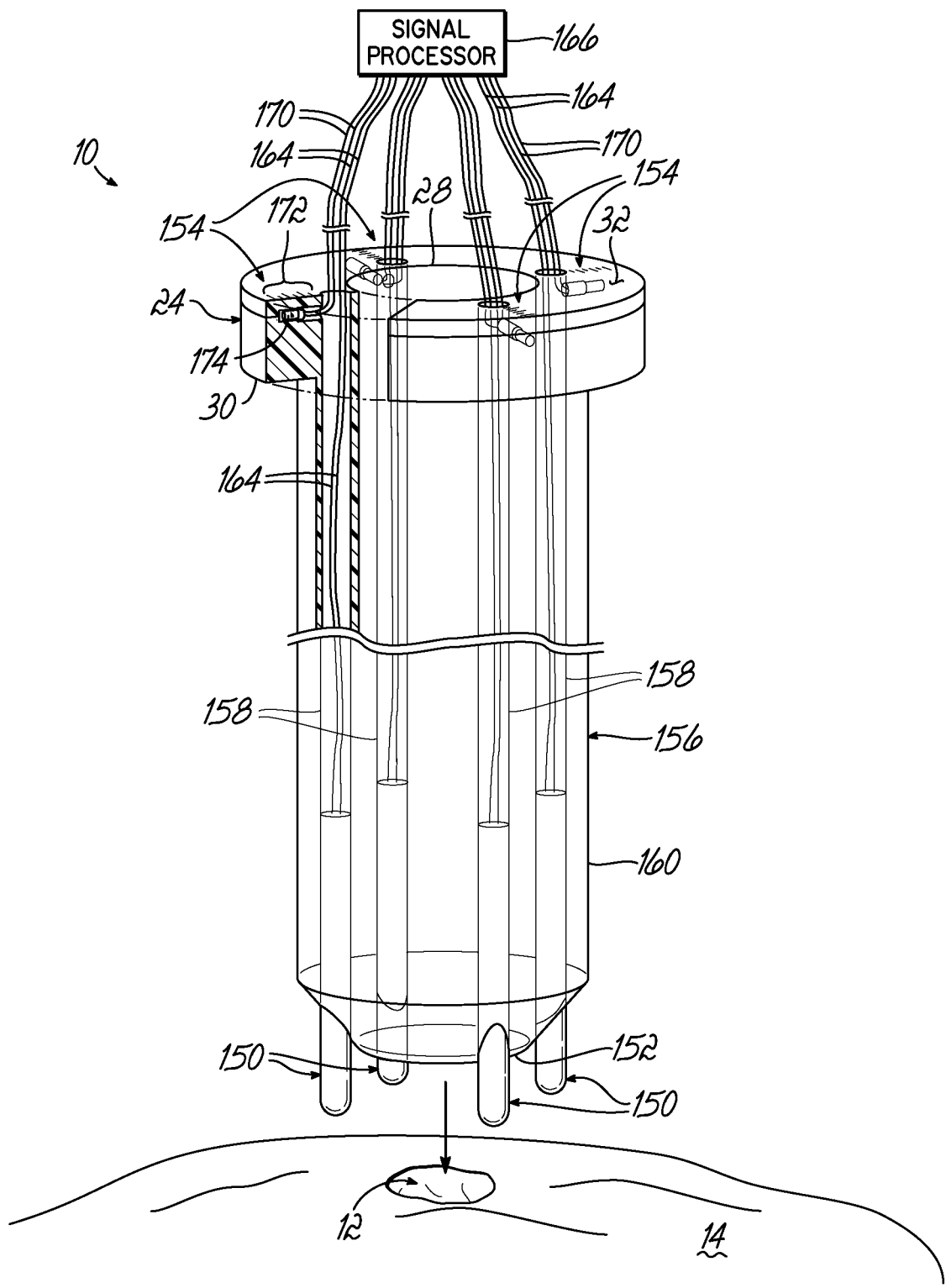
FIG. 6 is a perspective view, partially in cross-section, showing an instrument according to an embodiment in which the displacement of a probe is electrically communicated to an indicator.

FIG. 6 illustrates an embodiment in which the displacements of probes 150 relative to a first end 152 of a shaft 156 are electrically communicated to indicators 154. In this embodiment, each probe 150 is received in a corresponding first channel 158 defined in a wall 160 of the shaft 156. Each first channel 158 extends upwardly from the first end 152 in a generally vertical direction. Again, the first end 152 may be beveled to facilitate displacement of the probes 150 within the first channels 158 when the shaft 156 is brought into contact with the tissue surface 14.

The probes 150 may be any type of sensor configured to generate a signal corresponding to displacement. For example, each probe 150 may comprise a linear variable differential transformer (LVDT) that converts linear motion into corresponding electrical signals. Alternatively, each probe 150 may include a strain gauge or similar sensor that varies a property associated with an electrical signal (e.g., resistance) in proportion to the deformation and/or load experienced by the probe 150. In still other embodiments, a series of magnets (not shown) may be associated with each probe 150. The magnets generate a series of pulses when the probes 150 are displaced, and these pulses are associated with the corresponding displacements by a linear encoder.

Wires 164 coupled to the probes 150 communicate the electrical signals to a signal processor 166, which is schematically shown in FIG. 6. There may be a single signal processor 166 for all of the probes 150 or a plurality of signal processors 166 corresponding to the number of probes 150. Additionally, the signal processor 166 may be located in any suitable location, including within the wall 160 of the shaft 156, on the exterior of the shaft 156, or at a location remote from the shaft 156. For example, the instrument 10 may further include a transmitter and receiver (not shown) for wirelessly sending signals to and receiving signals from the signal processor 166.

The signal processor 166 in FIG. 6 is coupled to the indicators 154 by wires 170. After processing the signals received from the probes 150, the signal processor 166 generates displacement signals to operate the indicators 154. As mentioned above, any type of indicator configured to communicate the displacements of the probes 150 to a practitioner utilizing the instrument 10 may be used. Thus, it will be appreciated that the indicators 154 need not be positioned on the shaft 156 such that wires 170 are not required. For example, in a manner not shown herein, the indicators 154 may be located on a video monitor (not shown) viewed by the practitioner. The instrument 10 in such an embodiment may further include a transmitter to send electrical signals from the probes 150 to a receiver and/or processor associated with the video monitor. To this end, the indicators 154 may be operatively coupled (i.e., linked) to the probes 150 through wireless communication signals. Such an arrangement provides the practitioner with a "heads up" display.

Referring back to FIG. 6, the indicators 154 in the embodiment shown each comprise a displacement scale 172 provided on the upper surface 32 and an electrically actuated marking element 174 moveable along the displacement scale 172. The displacement signals sent by the signal processor 166 control the displacement of the electrically actuated marking elements 174. Thus, the position of the electrically actuated marking elements 174 along the displacement scales 172 generally indicate the displacement of the probes 150 relative to the first end 152 of the shaft 156. Although the electrically actuated marking elements 174 are each shown as a plunger element that serves the same function as the plunger element 96 (FIG. 4), any element capable of moving along the displacement scale 172 in response to electrical signals may be used.

Figure 7:
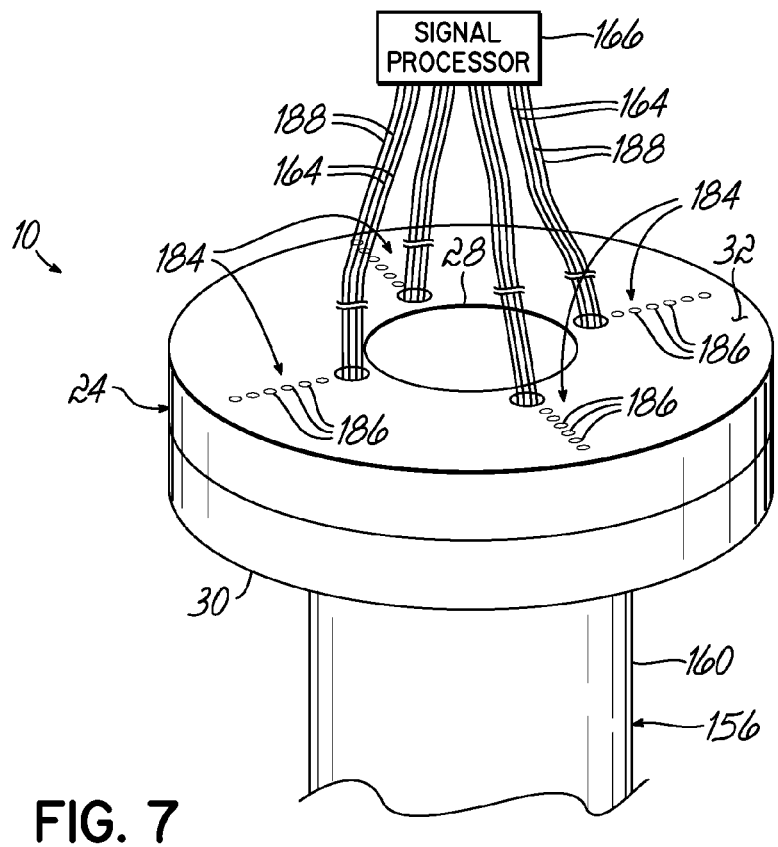
FIG. 7 is a perspective view of a portion of an instrument according to another embodiment in which the displacement of a probe is electrically communicated to an indicator.

In other embodiments, a moveable marking element is not required to communicate the displacements of the probes 150 to a practitioner. For example, FIG. 7 shows a plurality of indicators 184 each comprising a row of light sources 186, such as LED's, provided on the upper surface 32 of the shaft 156. Each row of light sources 186 is aligned above one of the probes 150 (FIG. 6), and each light source 186 represents a particular displacement of the associated probe 150 relative to the first end 152. The light sources 186 are electrically coupled to the signal processor 166 by wires 188 and operated in response to the displacement signals generated by the signal processor 166. Thus, as the probes 150 are moved in and out of the channels 158, different ones of the light sources 186 are operated (i.e., lit up) to visually communicate the displacements to a practitioner.

Although several representative embodiments are described above, those skilled in the art will appreciate that the displacement of the probes 40 (FIG. 1) relative to the first end 22 of the shaft 20, and/or the distance of the first end 22 relative to a tissue surface, may be communicated to the indicators 50 using other technologies and techniques. For example, the instrument 10 may further include laser measurement sensors (not shown) that communicate information of the probes 40 and/or first end 22 to the indicators 50. In other embodiments, the displacement of each probe 40 may be sonically or pneumatically communicated to the indicators 50. To this end, the instrument 10 may include sonic transmitters and receivers (not shown) disposed about the shaft 20 for measuring the relative distance between the first end 22 and a tissue surface. A combination of these arrangements may also be used in any particular embodiment. For example, the displacement of one probe 40 may be mechanically communicated to an indicator 50 while the displacement of another probe 40 may be electrically communicated to a different indicator 50. Alternatively, each probe 40 and channel 42 may be configured to operate as a hydraulic cylinder, and the instrument 10 may further include a pressure sensor (not shown) associated with the probe 40. Signals generated by the pressure sensor in response to displacement of the probe 40 are transmitted to the indicators 50 using a signal processor. Thus, in such an embodiment, each probe 40 incorporates aspects of the hydraulic and electrical communication discussed above with respect to the embodiments of FIGS. 3, 6, and 7.

With reference to FIGS. 8A-8F, a method of repairing a defect site 200 on a tissue surface 202 will now be described. The method involves using an instrument 204 similar to the instrument 10. However, to simplify matters, FIGS. 8A-8F do not illustrate the probes 40 and indicators 50 (FIG. 2) in detail. These elements are instead shown schematically in FIGS. 8A-8F because reference can be made to the description above for a more complete understanding of their operation. Indeed, those skilled in the art will appreciate that that the instrument 204 shown in FIGS. 8A-8F may incorporate any of the features described above.

Figure 8A:
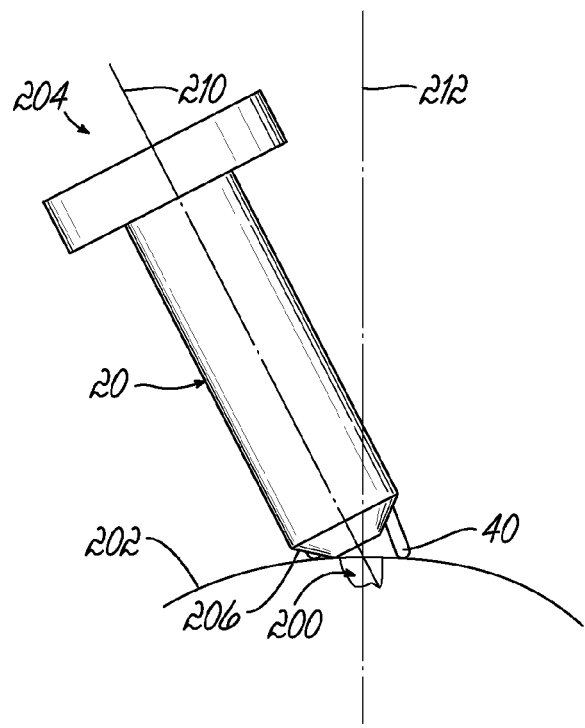
FIGS. 8A-8F are schematic view sequentially illustrating a method of repairing a defect site on a tissue surface using an instrument according to another embodiment.

The method begins by first positioning the instrument 204 proximate the patient's body. If the tissue surface 202 is subcutaneous, an incision (not shown) is made in the patient's skin to gain access to the defect site 200. The incision may be relatively small if the method is performed arthroscopically, or larger if the method is performed using mini-arthrotomy or open surgical techniques. An obturator (not shown) may be placed within the central bore 28 (FIG. 8C) to facilitate inserting the instrument 204 through the patient's skin regardless of which surgical technique is used. Prior to contact with the tissue surface 202, the probes 40 extend an initial distance beyond the first end 206 of the shaft 20. For example, the probes 40 may extend approximately 4 mm beyond the first end 206. Those skilled in the art will appreciate that this initial distance may vary among the probes 40, and may be set depending on the expected profile/geometry of the tissue surface 202. As shown in FIG. 8A, the instrument 204 is then moved toward the defect site 200, which may be a cavity or other irregularity on the tissue surface 202. The instrument 204 may be moved toward the defect site 200 at any angle because a desired orientation can later be established.

FIG. 8A illustrates the shaft 20 being substantially aligned along an axis 210 when the first end 206 is brought into contact with the tissue surface 202. The desired orientation for preparing the defect site 200 may be along a desired axis 212, which may be substantially perpendicular to a plane 214 tangent to the tissue surface 202 at the defect site 200, especially when the tissue surface 202 has a relatively large degree of curvature. Thus, the angle of the shaft 20 relative to the tissue surface 202 is then analyzed to determine if a change in orientation is required. This determination is made based upon displacement information communicated by the indicators 50.

Figure 8B:
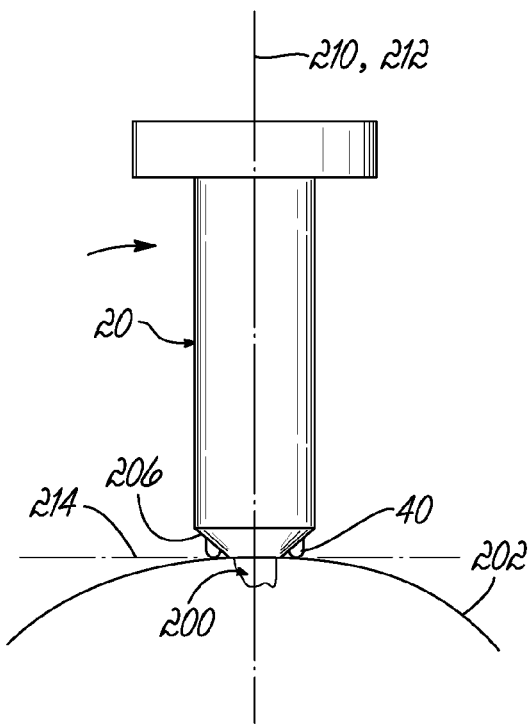
Figure 8C:
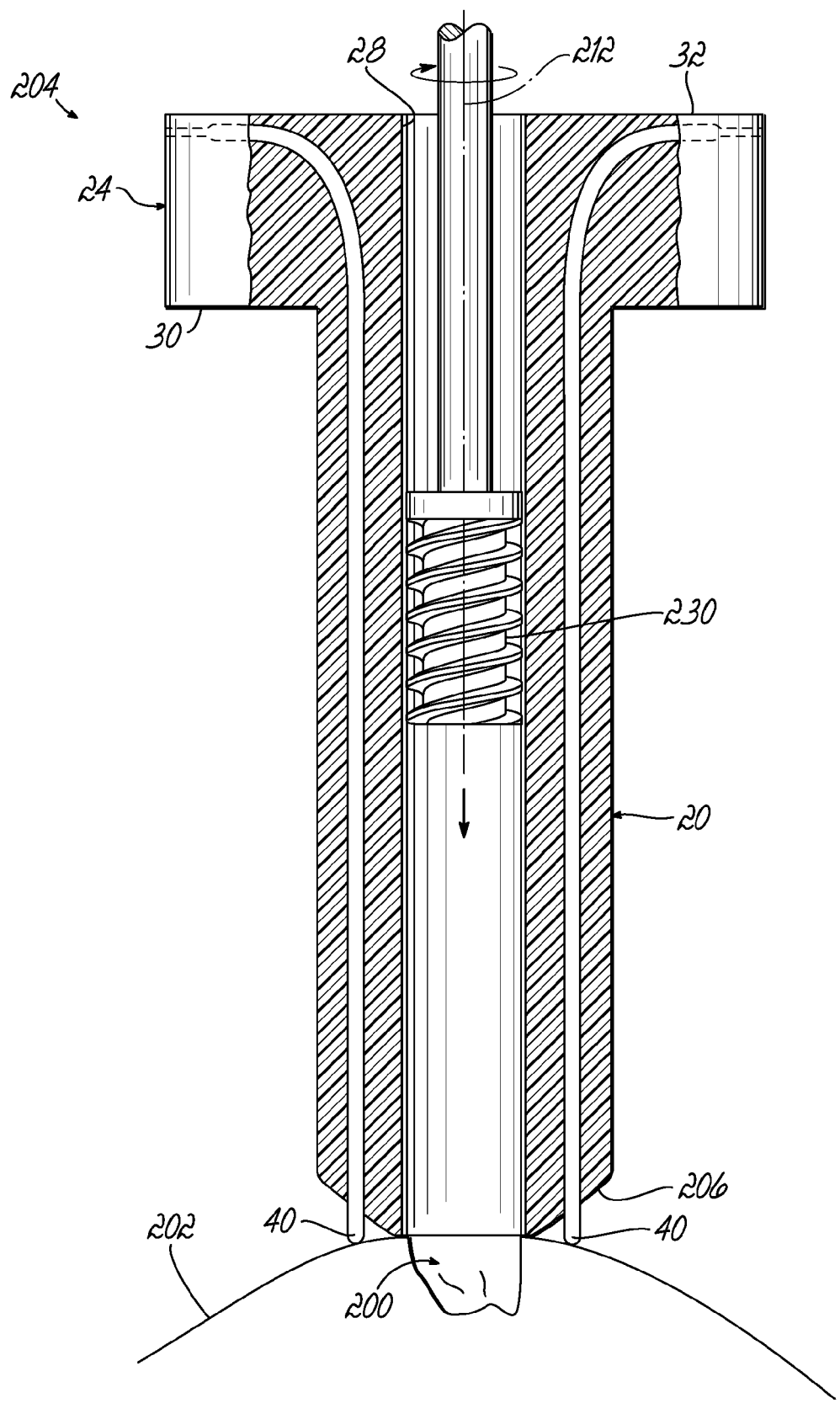

More specifically, when the first end 206 of the shaft 20 contacts the tissue surface 202, one or more of the probes 40 will also contact the tissue surface 202 and be displaced into the associated channel 42 (FIG. 8C). Arthroscopic or visual examination of the probes 40 may be performed after the instrument 204 is inserted into the patient's body to confirm that the probes 40 have unobstructed access to the tissue surface 202 surrounding the defect site 200. Unless the axis 210 is substantially aligned along the desired axis 212 after the shaft 20 contacts the tissue surface 202, the probes 40 will have different displacements relative to the first end 206. This displacement information is transmitted to the indicators 50 using any of the techniques described above. The indicators 50, in turn, communicate the displacement information to the practitioner. For example, the indicators 50 may display the displacement information using the displacement scales 52 (FIG. 2) or light sources 186 (FIG. 6).

As shown in FIGS. 8A and 8B, the practitioner may adjust the angle of the shaft 20 relative to the tissue surface 202. Moving the shaft 20 in such a manner will change the displacements of the probes 40 relative to the first end 206. When the axis 210 is substantially aligned with the desired axis 212, the displacements of the probes 40 may be approximately equal. This is because on articular cartilage or the like, the surface profile of the tissue surface 202 may approximate that of a sphere in the localized area around the defect site 200. However, to approximate alignment with the desired axis 212 even more accurately, each of the probes 40 may be spaced approximately 180° apart from another one of the probes 40. Such an arrangement enables the practitioner to compare the displacements between opposite probes 40 in the same plane to determine whether the angle of the shaft 20 relative to the tissue surface 202 should be adjusted in that particular plane.

Increasing the number of probes 40 spaced about the shaft 20 enables the practitioner to take into account a greater number of planes when making adjustments. In general, the greater number of planes (and, hence, probes 40) in which displacement is compared, the more effectively the surface profile of the tissue surface 202 is taken into account. Additionally, increasing the number of probes 40 produces a more reliable (i.e., repeatable) indication of perpendicularity. For example, when the surface profile of the tissue surface 202 is more effectively taken into account, the shaft 20 is more likely to have the same orientation when moved to the desired axis 212 (using the procedure described above) regardless of any rotation about the desired axis 212. When only discreet or localized information about the tissue surface 202 is provided, reliable/repeatable indications are more difficult to obtain.

Figure 8D:
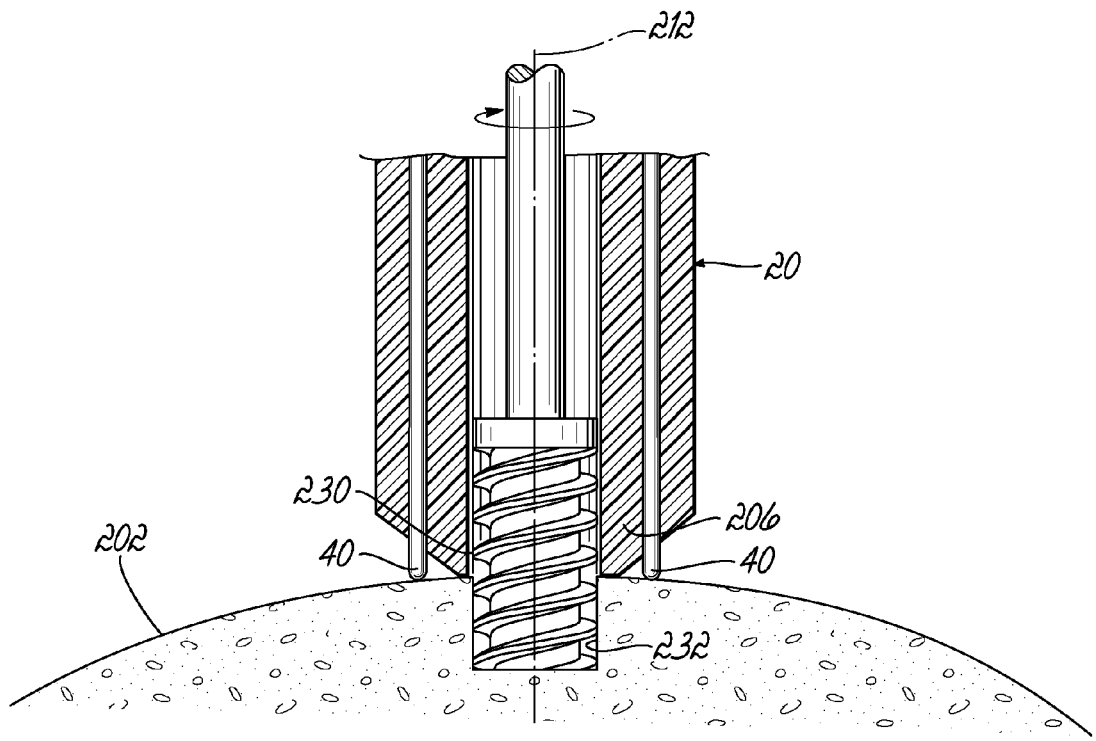

After making adjustments to properly orient the instrument 204, the practitioner maintains the shaft 20 at substantially the desired angle relative to the tissue surface 202. This may be accomplished manually by hand while monitoring the indicators 50 as necessary. An external support or fixation system (not shown) may also be provided to secure the instrument in the desired position once it is determined (e.g., similar to stereotactic procedures). As shown in FIGS. 8C and 8D, a defect preparation tool 230 may then be inserted through the central bore 28 and toward the defect site 200. Although the defect preparation tool 230 is shown as a drill, any other device configured to prepare a defect to receive an implant 240 (FIG. 8E) may be used. Other examples of suitable defect preparation tools include, without limitation: punches, curettes, reamers, and picks.

Figure 8E:
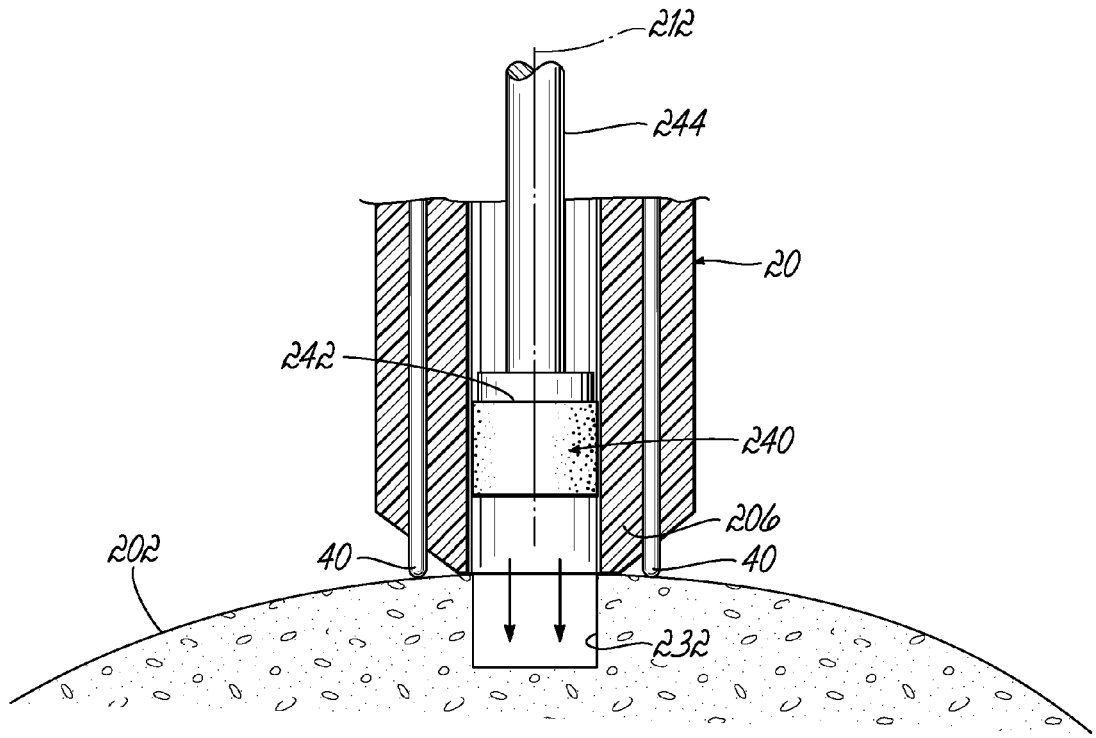

The defect preparation tool 230 is configured to prepare the defect site 200 to a desired size, shape, and/or depth for receiving the implant 240. For example, the defect preparation tool 230 may form a cavity 232 having a size and shape generally corresponding to the implant 240. After preparing the defect site 200, the defect preparation tool 230 may be removed from the central bore 28. The central bore 28 may then serve as a conduit for the removal of any debris. Additionally, as shown in FIG. 8E, the implant 240 may be inserted into the central bore 28 and delivered to the defect site 200 through the shaft 20. The implant 240 is pushed through the shaft 20 using a driving tool 244.

Again, throughout the procedure, the shaft 20 may be maintained at a desired angle relative to the tissue surface 202 by monitoring the displacement information displayed by the indicators 50. The implant 240 is advantageously delivered along the same axis along which the defect preparation tool 230 was aligned when forming the cavity 232. Such a procedure facilitates delivering the implant 240 so that the implant 240 may be fully seated within the cavity 232.

Figure 8F:
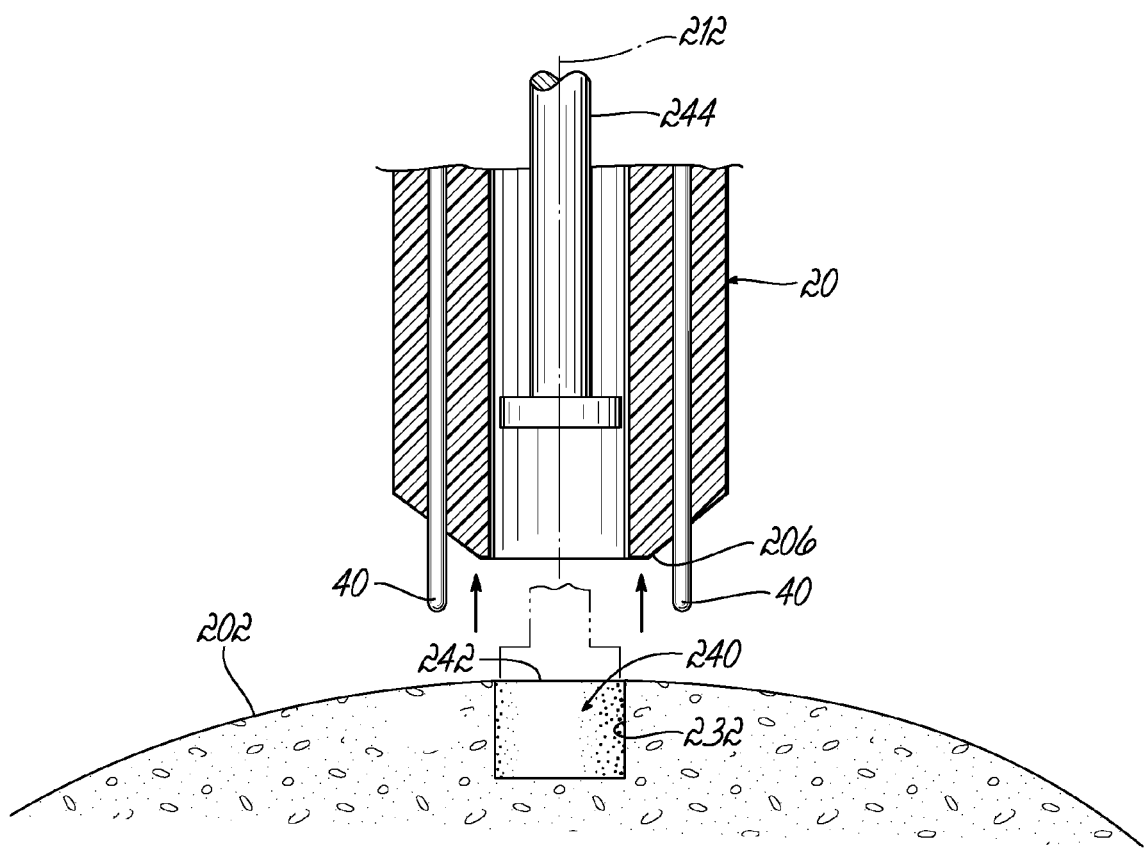

As shown in FIG. 8F, the driving tool 244 and instrument 204 are eventually moved away from the tissue surface 202 when the procedure is complete. Because the cavity 232 was prepared at an angle substantially perpendicular to a tangent of the tissue surface 202 at the defect site 200, a top surface 242 of the implant 240 may be substantially flush with the tissue surface 202 when fully seated within the cavity 232. Such an arrangement facilitates integration of the implant 240 to effectively treat the defect site 202. In particular, the implant 240 effectively occupies the defect site 200 so that there remains no substantial cavities or depressions relative to the surrounding tissue surface 202. Additionally, the absence of implant portions abruptly extending above the tissue surface 202 reduces or eliminates the risk of displacement or premature wear on the implant 240.

As a variation of the method described above, the instrument 204 or an additional harvesting instrument (not shown) that operates upon the same principles may be used to locate a similarly-shaped tissue surface after "mapping" the curvature of the tissue surface 202 and preparing the defect site 200. For example, after the instrument 204 is aligned with the desired axis 212, the displacement information is recorded, stored, committed to memory, or otherwise retained by the practitioner. The practitioner then attempts to match this displacement information when using the instrument 204 or harvesting instrument to select a remote tissue surface from which to harvest the implant 240. The remote tissue surface may be on the patient or a donor. Once a similarly-shaped remote tissue surface is located, the instrument 204 or harvesting instrument is used to cut or extract the implant 240 from the remote tissue surface. To this end, the instrument 204 or harvesting instrument may include a blade associated with its shaft 20. Alternatively, a separate cutting device or similar tool for extracting the implant 240 from the remote tissue surface may be inserted through the central bore 28.

The implant 240 is eventually delivered to the cavity 232 at the defect site 200 in the manner described above. Because the implant 240 was harvested from a remote tissue surface having the same or similar profile as the tissue surface 202, the top surface 242 of the implant 240 is more likely to approximate the natural curvature of the tissue surface 202.

While several embodiments are described above in considerable detail, the inventors do not intend to restrict or in any way limit the scope of the appended claims to such detail. Additional advantages and modifications will readily appear to those skilled in the art. For example, although the probes 40 described above move within the channels 42 formed in the shaft 20, the probes 40 may alternatively be located within tubes (not shown) provided on the exterior or interior of the shaft 20. Furthermore, those skilled in the art will appreciate that two or more of the components discussed above may be provided as part of assembly. For example, the assembly may include both the instrument 10 and the defect preparation tool 230. Alternatively or additionally, the assembly may include both the instrument 10 and the implant 240. The defect preparation tool 230 and/or implant 240 may be designed to effectively cooperate with the central bore 28 of the shaft 20 when provided as part of an assembly.

The invention in its broader aspects is thus not limited to the specific details, representative apparatus and methods, and illustrative examples shown and described. Accordingly, departures may be made from such details without departing from the scope or spirit of the general inventive concept.

What is claimed is:

1. An instrument for determining the proper orientation for repairing a defect site on a tissue surface, comprising:
 a shaft having a first end configured to contact the tissue surface, a second end opposite the first end, and a central bore defined by an outer wall extending between the first and second ends, the outer wall having a plurality of channels defined therein;
 a plurality of probes operatively coupled to the shaft, each probe being slidably disposed within one of the channels in the outer wall of the shaft and including a first end configured to extend past the first end of the shaft and a second end configured to be contained without the second end of the probe extending beyond the second end of the shaft;
 a biasing member operatively coupled to each of the probes, the biasing members configured to actively bias the first end of the probe past the first end of the shaft and to allow displacement of the second end of the probe within the channel in which the probe is disposed; and
 at least one indicator operatively coupled to the plurality of probes, the at least one indicator being configured to display the displacements of the probes relative to the first end so that the displacements of the probes may be compared.

2. The instrument of claim 1 wherein the probes are substantially equally spaced about a periphery of the shaft.

3. The instrument of claim 1 wherein at least a portion of the shaft is substantially cylindrical and each probe is spaced approximately 180 degrees apart from another one of the probes.

4. The instrument of claim 3, wherein the plurality of probes includes first, second, third, and fourth probes spaced at 90 degree angles about the periphery of the shaft, and wherein the at least one indicator comprises first, second, third, and fourth indicators operatively coupled to first, second, third, and fourth probes, respectively.

5. The instrument of claim 1 wherein the at least one indicator comprises a plurality of indicators each configured to display to the displacement of a corresponding one of the probes.

6. The instrument of claim 1 wherein the biasing members are springs.

7. The instrument of claim 5 wherein the first end of the shaft has a first outer diameter and the second end has a second outer diameter greater than the first outer diameter so as to define a flange portion at the second end, the flange portion terminating in an upper surface, the plurality of channels each extending into the flange portion and including an upper portion visible through the upper surface, and each indicator comprising a displacement scale provided on the upper surface proximate the upper portion of one of the channels.

8. The instrument of claim 5 wherein the outer wall is beveled at the first end.

9. The instrument of claim 1 wherein the tissue surface comprises at least one of the following: a bone surface, a cartilage surface, a skin surface, or a dental surface.

10. The instrument of claim 1, further comprising:
 a plurality of fluid channels operatively coupling the plurality of probes to the at least one indicator;
 wherein the displacements of the probes are hydraulically communicated to the at least one indicator by the fluid channels.

11. The instrument of claim 10 wherein each probe comprises a plunger element that seals, engages, and moves within one of the fluid channels.

12. The instrument of claim 10 wherein the at least one indicator comprises a plurality of indicators each configured to display the displacement of one of the probes.

13. The instrument of claim 1 wherein the displacement of each probe relative to the first end is mechanically communicated to the at least one indicator.

14. The instrument of claim 13, wherein each channel includes an upper portion visible through an outer surface of the shaft, the at least one indicator comprising a plurality of indicators each including a displacement scale provided on the shaft proximate to one of the upper portions, and the probes each comprising an elongated element received in the corresponding channel and having a tip portion configured to contact the tissue surface and an end portion opposite the tip portion, wherein the end portion communicates the displacement of the tip portion to the corresponding displacement scale.

15. The instrument of claim 14 wherein the end portion of each elongated element includes a scribe configured to move along the corresponding displacement scale when the associated tip portion moves relative to the shaft.

16. The instrument of claim 14 wherein at least a first portion of each elongated element comprises a first material and at least a second portion of each elongated element comprises a second material, the second material being less rigid than the first material.

17. The instrument of claim 13, further comprising:
 a plurality of levers configured to communicate the displacements of the plurality of probes to the at least one indicator, each lever further configured to amplify the displacements communicated to the at least one indicator.

18. The instrument of claim 1 wherein the displacement of each probe relative to the first end is pneumatically communicated to the at least one indicator.

19. An instrument for repairing a defect site on a tissue surface, comprising:
 a shaft having a first end configured to contact the tissue surface, a second end opposite the first end, and a central bore defined by an outer wall extending between the first and second ends, the outer wall having a plurality of channels defined therein;
 a plurality of probes each slidably disposed within one of the channels in the outer wall of the shaft and extending an initial distance beyond the first end, each probe being configured to move relative to the shaft so as to be displaced when the first end contacts the tissue surface;
 a biasing member operatively coupled to each of the probes, the biasing members configured to allow displacement of the probes within the channels; and
 a plurality of indicators corresponding to the plurality of probes, each indicator being configured to display information related to the displacement of a corresponding one of the probes when the first end of the shaft contacts the tissue surface.

20. The instrument of claim 19 wherein at least a portion of the shaft is substantially cylindrical and each probe is spaced approximately 180 degrees apart from another one of the probes.

21. An assembly for repairing a defect site on a tissue surface, comprising:
 a positioning instrument, comprising:
  a shaft having a first end configured to contact the surface of the tissue and a second end opposite the first end, wherein the shaft is a cannula defined by an outer wall surrounding a central bore, the outer wall having a plurality of channels defined therein;

a plurality of probes operatively coupled to the shaft, each probe being slidably disposed within one of the channels in the outer wall of the shaft and including a first end configured to extend past the first end of the shaft and a second end configured to be contained without the second end of the probe extending beyond the second end of the shaft;

a biasing member operatively coupled to each of the probes, the biasing members configured to actively bias the first end of the probe past the first end of the shaft and to allow displacement of the second end of the probe within the channel in which the probe is disposed; and at least one indicator operatively coupled to the plurality of probes, the at least one indicator being configured to display the displacements of the probes relative to the first end so that the displacements of the probes may be compared; and a defect preparation tool configured for displacement in the central bore of the shaft and configured to prepare the defect site for receiving an implant.

22. The assembly of claim 21 wherein the defect preparation tool is configured to extend through the central bore of the shaft.

23. The assembly of claim 21 wherein the defect preparation tool comprises at least one of the following: a drill, a punch, a curette, a reamer, or a pick.

24. The assembly of claim 21 wherein the shaft is transparent to allow visualization of the defect site and implant.

25. The assembly of claim 21 wherein the at least one indicator comprises a plurality of indicators each configured to display to the displacement of a corresponding one of the probes.

26. The assembly of claim 21 wherein the biasing members are springs.

27. The assembly of claim 21 wherein the probes are substantially equally spaced about a periphery of the shaft.

28. The assembly of claim 21, further comprising:

an implant configured to be received within the central bore of the shaft and delivered to the defect site through the central bore.

29. An assembly for repairing a defect site on a tissue surface, comprising:

a positioning instrument, comprising:

a shaft having a first end configured to contact the surface of the tissue and a second end opposite the first end, wherein the shaft is a cannula defined by an outer wall surrounding a central bore, the outer wall having a plurality of channels defined therein;

a plurality of probes operatively coupled to the shaft, each probe being slidably disposed within one of the channels in the outer wall of the shaft and including a first end configured to extend past the first end of the shaft and a second end configured to be contained without the second end of the probe extending beyond the second end of the shaft;

a biasing member operatively coupled to each of the probes, the biasing members configured to actively bias the first end of the probe past the first end of the shaft and to allow displacement of the second end of the probe within the channel in which the probe is disposed;

at least one indicator operatively coupled to the plurality of probes, the at least one indicator being configured to display the displacements of the probes relative to the first end so that the displacements of the probes may be compared; and an implant configured to be received within the central bore of the shaft and delivered to the defect site through the central bore.

30. The assembly of claim 29 wherein the biasing members are springs.

* * * * *